United States Patent
McKinlay et al.

(10) Patent No.: US 10,961,263 B2
(45) Date of Patent: *Mar. 30, 2021

(54) CELL-PENETRATING, GUANIDINIUM-RICH OLIGOPHOTRIESTERS FOR DRUG AND PROBE DELIVERY

(71) Applicant: The Board of Trustees of the Leland Stanford Junior University, Stanford, CA (US)

(72) Inventors: Colin J. McKinlay, Atherton, CA (US); Paul A. Wender, Menlo Park, CA (US); Robert M. Waymouth, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/844,304

(22) Filed: Apr. 9, 2020

(65) Prior Publication Data

US 2020/0308200 A1 Oct. 1, 2020

Related U.S. Application Data

(63) Continuation of application No. 15/773,725, filed as application No. PCT/US2016/061515 on Nov. 11, 2016, now Pat. No. 10,654,875.

(60) Provisional application No. 62/254,653, filed on Nov. 12, 2015.

(51) Int. Cl.
| | |
|---|---|
| C07F 9/09 | (2006.01) |
| C07F 9/655 | (2006.01) |
| A61K 47/58 | (2017.01) |
| A61K 47/54 | (2017.01) |
| A61K 31/337 | (2006.01) |

(52) U.S. Cl.
CPC .......... *C07F 9/098* (2013.01); *A61K 31/337* (2013.01); *A61K 47/548* (2017.08); *A61K 47/605* (2017.08); *C07F 9/091* (2013.01); *C07F 9/65512* (2013.01)

(58) Field of Classification Search
None
See application file for complete search history.

(56) References Cited

U.S. PATENT DOCUMENTS 10,654,875 B2 * 5/2020 McKinlay .......... C07F 9/65512
2008/0004234 A1   1/2008 Segev

FOREIGN PATENT DOCUMENTS

WO   2010056403   5/2010

OTHER PUBLICATIONS

Stanzl et al., "15 Years of Cell-penetrating, Guanidinium-rich Molecular Transporters: Basic Science, Research Tools, and Clinical Applications", Acc Chem Res., Dec. 17, 2013, pp. 1-18, 46(12), ACS Publications, Washington, DC.
Wender et al., "The design of guanidinium-rich transporters and their internalization mechanisms", Adv Drug Deliv Rev., Mar. 1, 2008, pp. 452-472, 60(4-5), Elsevier, New York City, NY.
Wender et al., "Guanidinium-Rich, Glycerol-Derived Oligocarbonates: A New Class of Cell-Penetrating Molecular Transporters That Complex, Deliver, and Release siRNA", Mol. Pharm., Mar. 2, 2015, pp. 742-750, 12(3), ACS Publications, Washington, DC.
Inami et al (1996) "Synthesis of monooleoyl glycerophospho heptapeptide candidate of pathogen of essential hypertension", Bioorganic & Medicinal Chemistry Letters, Pergamon, Amsterdam, NL, vol. 6, No. 6, pp. 601-604.
McKinlay et al (2016) "Cell-Penetrating, Guanidinium-Rich Oligophosphoesters: Effective and Versatile Molecular Transporters for Drug and Probe Delivery", Journal of the American Chemical Society, val. 138, No. 10, pp. 3510-3517.

* cited by examiner

*Primary Examiner* — Joseph R Kosack
(74) *Attorney, Agent, or Firm* — Pamela J. Sherwood; Bozicevic, Field & Francis LLP

(57) ABSTRACT

Guanidinium-rich oligophosphotriesters transporter compounds and methods of making and using the same are provided. Also provided are pharmaceutical compositions that include the subject transporter compounds, where the transporter can be joined to a cargo of interest, and is formulated with a pharmaceutically acceptable excipient. Formulations may be provided in a unit dose, where the dose provides an amount of the compound effective to afford a desired therapeutic effect. Methods of using the subject transporter compounds to deliver a cargo moiety to a cell are provided, where the method can include contacting a target cell with the transporter compound. The subject methods can be performed in vitro or in vivo.

14 Claims, 11 Drawing Sheets
(1 of 11 Drawing Sheet(s) Filed in Color)

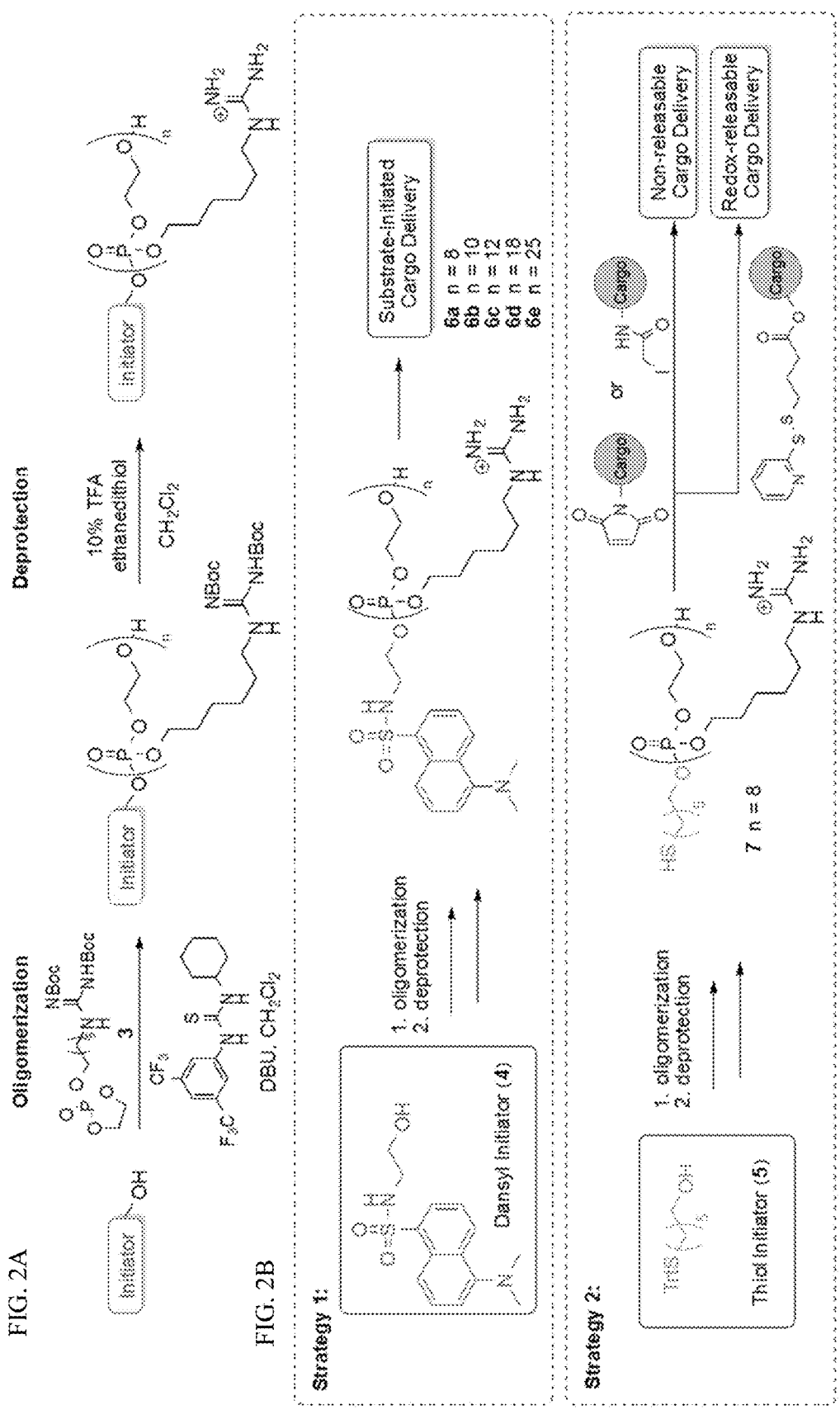

CELL-PENETRATING, GUANIDINIUM-RICH OLIGOPHOSPHOTRIESTERS FOR DRUG AND PROBE DELIVERY

CROSS-REFERENCE

This application claims benefit and is a continuation of 371 application Ser. No. 15/773,725, filed May 4, 2018, which claims benefit of PCT Application No. PCT/US2016/061515, filed Nov. 11, 2016, which claims benefit of U.S. Provisional Patent Application No. 62/254,653, filed Nov. 12, 2015, which application are incorporated herein by reference in their entirety.

FEDERALLY SPONSORED RESEARCH AND DEVELOPMENT

This invention was made with Government support under contract 1306730 awarded by the National Science Foundation and under contracts CA031841 and CA031845 awarded by the National Institutes of Health. The Government has certain rights in the invention.

BACKGROUND

The development of new strategies and agents that provide for and enhance the passage of drugs and probes across biological barriers is a goal of unsurpassed significance in research, imaging, diagnostics, and therapy. Many potential drug candidates are abandoned during development simply because they do not possess the proper physical properties needed for formulation and to reach their targets. Other drug candidates are not even pursued because they are perceived to have problematic physical properties. Collectively, this restricts the universe of possible drug candidates to the limited few with optimal physical properties. For these drug candidates and more generally for many research tools, therapeutic leads and diagnostic agents, improved and highly effective delivery strategies are necessary.

The HIV Tat 9-mer (RKKRRQRRR), a polar (oligocationic) peptide, can cross non-polar cell membranes as a function of the number and spatial array of its guanidinium groups. Such agents, dubbed "guanidinium-rich molecular transporters", are proposed to act as physical property "chameleons", transitioning from polar oligocations to less polar, cell-penetrating complexes as they engage cell-surface anions in electrostatic and bifurcated hydrogen-bonding interactions. Compositionally diverse guanidinium-rich scaffolds, including peptoids, spaced peptides, oligocarbamates, dendrimers, and oligocarbonates are able to efficiently enter cells, including guanidinium-rich modified[10-12] and cyclic peptides[13,14], peptide nucleic acids,[15] and transporters resulting from the oligomerization of guanidinium-containing monomers such as norbornenes, methacrylamides, and cyclic disulfides. These transporters can enhance the passage of numerous cargos including small molecules, peptides, and oligonucleotides, across multiple biological barriers including the cell wall of algae.

SUMMARY OF THE DISCLOSURE

The design, synthesis, and biological evaluation of a new family of highly effective cell-penetrating molecular transporters, guanidinium-rich oligophosphoesters, are described. Compounds of the present disclosure may have a formula (I) as follows:

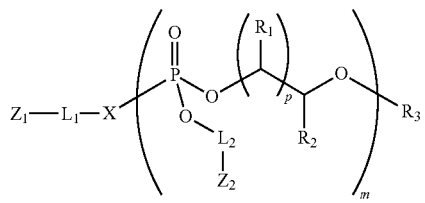

where $Z_1$ is a cargo moiety, a reactive functional group or a protected functional group; $L_1$ is an optional linker; X is O, S, NH or $CH_2$; each $L_2$ is a linker; each $Z_2$ is an guanidine group or a protected guanidine group; $R_3$ is H, an alkyl, a substituted alkyl, an acyl, a substituted acyl, an aryl, a substituted aryl, a heteroaryl or a substituted heteroaryl; each $R_1$ and $R_2$ are independently H, an alkyl or a substituted alkyl; each p is independently 1, 2 or 3; and m is 50 or less. In some instances, the molecules of the invention may include a structure:

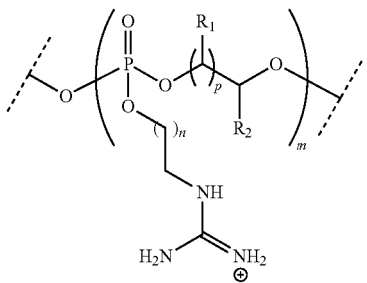

where n is from about 4 to about 25 units in length, m from about 8 to about 20 units in length, and p is from 1 to about 3 units in length.

The guanidinium-rich oligophosphotriesters may be joined either covalently or non-covalently to a cargo moiety of interest for delivery into a cell, including without limitation small molecule drugs including without limitation chemotherapeutic agents, peptides, polynucleotides, proteins, siRNA, mRNA, plasmids, metals, imaging agents, sensors and the like. In some designed cases, transporters of certain lengths and functionalities have been demonstrated to have inherent biological activity, so these molecules can be used as cell-penetrating therapeutics as such, or in combination therapy with an attached cargo. The terminal groups, $R_1$ and $R_2$ may be selected from moieties described herein, for example at paragraphs 68-81.

Unexpectedly, these new transporters are superior in cell uptake to previously studied guanidinium-rich oligocarbonates and oligoarginines, showing over 2-fold higher uptake than the former and 7-fold higher uptake than the latter. In addition to drug/probe attachment as initiators in the oligomerization process, initiation with a protected thiol gives, upon deprotection, thiol-terminated transporters which can be thiol-click conjugated to a variety of probes, drugs and other cargos as exemplified by the conjugation and delivery of the probe fluorescein-maleimide and the medicinal agent paclitaxel (PTX) into cells. Of particular significance given that drug resistance is a major cause of chemotherapy failure, the PTX-transporter conjugate, designed to evade Pgp export and release free PTX after cell entry, shows efficacy against PTX-resistant ovarian cancer cells. Collectively this study introduces a new and highly effective class of guanidinium-rich cell-penetrating transporters and methodology for their step-economical (one step) conjugation to drugs and probes, and demonstrates that the resulting drug/probe-conjugates readily enter cells, outperforming previously reported guanidinium-rich oligocarbonates and peptide transporters.

The compositions find use in therapeutic delivery. The inventive phosphotriester oligomers are effective for delivering bioactive therapeutic agents that would normally not posess the physical properties necessary to penetrate cells. This expands the chemical space available as "druggable molecules" and provides development of new diverse targets. Additionally, this delivery technology can be used to increase the efficacy of existing therapies, for example through the delivery of antibiotic conjugates directly to bacterial cells. The addition of a transporter to therapeutic molecules can additionally improve formulation properties hydrophobic drug molecules, meaning that highly nonpolar molecules can be administered in much less time, and much smaller volumes than existing treatments.

Diagnostic Imaging: The phosphotriester oligomers show promise in delivering imaging agents into cells. By attaching an imaging probe (fluorescent, bioluminescent, magnetic, PET agent, etc) as the cargo molecule, phosphotriester oligomers can be used for molecular imaging, enabling localization of a reporter molecule inside of cells. By combining this technology with numerous available targeting strategies, specific cell or tissue types can be imaged, allowing for identification of cancerous areas, or detection of foreign cells such as bacteria or parasites.

Visualization of surgical procedures: Administration of fluorescent transporters which can be activated in tumor tissues can be used as a visualization tool during surgical procedures. Fluorescent tagging of tumor cells provides and simplifies resection of tumor margins and increases efficacy of surgical procedures.

Treatment of resistant disease: Guanidinium-rich transporters, including these phosphotriesters have been shown to restore the efficacy of resistance-prone drugs such as paclitaxel (PTX). By appending PTX to phosphotriester transporters using a releasable disulfide linkage, the mechanism of cellular entry is altered such that PTX is no longer a substrate for drug efflux pumps which are a major cause of drug resistance. Guanidinium-rich phosphotriester oligomers of PTX, for example, effective against an engineered PTX-resistant cell lines and maintain cytotoxicity even when free PTX is no longer effective.

Additional Applications: Targeting transporters to tumors, organs, or tissues using external or enzymatic activation. Formulation as a cationic gene carrier for oligonucleotides including plasmid DNA, mRNA, and siRNA. Penetration of new barriers including the blood brain barrier, algal cell wall, bacterial cell membrane and/or cell wall, skin, etc.

Slow Release from Drug Depots: These delivery vehicles can be used for the design of biodegradable materials for the slow release of biologically active molecules from drug depots or implants. By forming a hydrogel with the cationic transporter oligomers and entrapping a drug molecule, bolus injections can be avoided using solid or gel-like materials.

Localized Treatment: Because transporters can be designed to rapidly adhere to tissues, they can be used to retain drugs near the site of administration. By appending a drug molecule to the transporter and injecting in a target area, the drug may afford fewer off-target affects associated with diffusion of the drug away from the injection site.

Decorating of Nanoparticles for Increased Uptake: Functionalization of macromolecular nano- or microparticles (e.g. micelles, liposomes, protein vaults, metallic nanoparticles, quantum dots, or virus capsids) with oligomers can increase their uptake, allowing these other structures to reach their intracellular targets more efficiently.

Potential Activity of Transporter Molecules: In some designed cases, transporters of certain lengths and functionalities have been demonstrated to have inherent biological activity, such as antibacterial properties. These molecules can be used as cell-penetrating therapeutics as such, or in combination therapy with an attached cargo.

These and other advantages, and features of the disclosure will become apparent to those persons skilled in the art upon reading the details of the compositions and methods of use more fully described below.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 2A-2B. Overview of synthetic methodologies employed to access guanidinium-rich oligophosphoester transporters. (FIG. 2A) OROP of a cyclic phospholane monomer for two-step access to guanidinium-functionalized oligophosphoesters for drug/probe delivery. (FIG. 2B) Methods of incorporation of drug or probe molecules onto cell-penetrating oligomers. Strategy 1: Initiation of oligomerization by drugs or probes containing a primary alcohol, such as the dansyl initiator (4). Strategy 2: Initiation of oligomers by trityl-mercaptohexanol (5) to produce, upon deprotection, oligomers containing a free thiol which can be conjugated to a variety of thiol-reactive drugs/probes, or attached through a redox-cleavable disulfide bond to form releasable drug conjugates.

(FIG. 3A) Length dependence of uptake of Dansyl-HexPhos oligomers 6a-e in HeLa cells compared to Dansyl-Arg8 (8) and Dansyl-MTC-G8 (9). Cells were treated at 10 µM for 10 minutes. Fluorescence values are the mean of 10,000 events recorded by flow cytometry and are normalized to background fluorescence of untreated cells. (FIG. 3B) Cell line dependence of uptake of HexPhos8 in HeLa cells (1) Jurkat cells (2) OVCA429 cells (3) and mouse 4T1 cells (4). Values reported are the mean fluorescence for 10,000 events recorded by flow cytometry. All values are the average of at least three separate experiments, with error bars representing standard deviation. (FIG. 3C) Structures of previously reported transporter systems Dansyl-Arg8 (8) and Dansyl-MTC-G8 (9).

(FIG. 4A) Delivery of FL-maleimide to HeLa cells by click-coupling to thiol-initiated HexPhos oligomer 8. Maleimide control and HexPhos8 conjugate (11 and 12 respectively) were formed by reaction of 10 with the corresponding thiol for 2 hours at room temperature in PBS.

The resulting compounds were exposed to HeLa cells at 10 µM final concentration for 10 minutes before determining uptake by flow cytometry. Data shown is the average fluorescence of 10,000 events measured. All values are the result of three separate experiments, with error bars representing the standard deviation. (FIG. 4B) Representative flow cytometry histogram showing a complete shift in population fluorescence for cells treated with FL-HexPhos conjugate 12. (FIG. 4C) Structures of compounds used for FL-maleimide delivery.

DEFINITIONS

Figure 1:
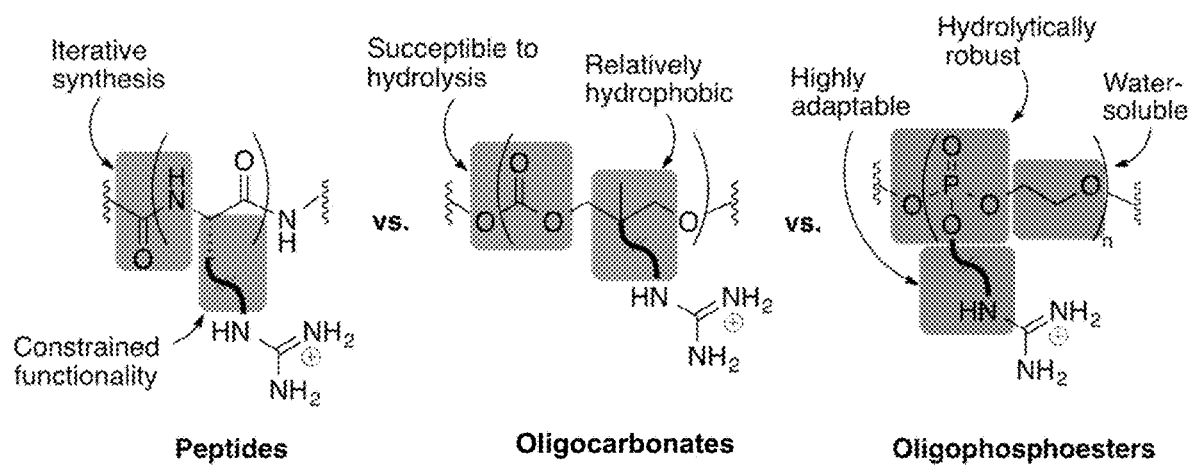
FIG. 1. Comparison of select oligomeric scaffolds for drug delivery to the oligophosphoesters described in this work, specifically highlighting ease of synthesis, backbone hydrophilicity, structural diversity, and aqueous stability.

Before embodiments of the present disclosure are further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Any methods and materials similar or equivalent to those described herein can also be used in the practice or testing of embodiments of the present disclosure.

It must be noted that as used herein and in the appended claims, the singular forms "a", "and", and "the" include plural referents unless the context clearly dictates otherwise. Thus, for example, reference to "a compound" includes not only a single compound but also a combination of two or more compounds, reference to "a substituent" includes a single substituent as well as two or more substituents, and the like.

In describing and claiming the present invention, certain terminology will be used in accordance with the definitions set out below. It will be appreciated that the definitions provided herein are not intended to be mutually exclusive. Accordingly, some chemical moieties may fall within the definition of more than one term.

As used herein, the phrases "for example," "for instance," "such as," or "including" are meant to introduce examples that further clarify more general subject matter. These examples are provided only as an aid for understanding the disclosure, and are not meant to be limiting in any fashion.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As used herein, the terms "oligomerization" and "polymerization" are used interchangeably and refer to a polymerization reaction whereby two or more monomers are combined to produce an oligomer or polymer product. As used herein, the terms "oligomer" and "polymer" are used interchangeably.

As used herein, the term "monomer" is used to refer to either the starting monomer reagent suitable for use in a oligomerization reaction, or to refer to one of the monomer units of an oligomer or polymer. As used herein, the term "sidechain" refers to the group of the monomer that branches from the backbone of a product oligomer.

The terms "individual," "host," "subject," and "patient" are used interchangeably herein, and refer to an animal, including, but not limited to, human and non-human primates, including simians and humans; rodents, including rats and mice; bovines; equines; ovines; felines; canines; and the like. "Mammal" means a member or members of any mammalian species, and includes, by way of example, canines; felines; equines; bovines; ovines; rodentia, etc. and primates, e.g., non-human primates, and humans. Non-human animal models, e.g., mammals, e.g. non-human primates, murines, lagomorpha, etc. may be used for experimental investigations.

As used herein, the terms "determining," "measuring," "assessing," and "assaying" are used interchangeably and include both quantitative and qualitative determinations.

As used herein, the term cargo moiety refers to any compound that is of interest for delivery to a cell. Cargo moieties of interest include without limitation small molecule drugs including without limitation chemotherapeutic agents, peptides, polynucleotides, proteins, siRNA, mRNA, plasmids, metals, imaging agents, sensors and the like. Cargo moieties of interest include, but are not limited to, small drug molecules, fluorescent/radioactive/optical imaging agents, peptides/proteins/enzymes, nucleic acids (siRNA/RNA/DNA/etc.), metal based compounds/catalysts, polymers, site-specific cellular targeting agents (compounds/ligands/antibodies/etc.), etc. for diverse applications such as chemotherapeutic agents, smart adjuvants, gene therapy vectors, biosensors, bioreactors, and so forth. Exemplary cargo moieties of interest include, but are not limited to: Small drug molecules, such as paclitaxel, doxorubicin, cisplatin, and bryostatin, etc; Peptides, such as pVI (adenovirus lytic domain), TAT (HIV lytic domain), ovalbumin, and NS5A1-31 (Hep C viral membrane anchor), etc.; Proteins, such as GFP, MOMP (chlamydia protein), and EGF/EGFR, antibodies, etc.; Metals and metal ions such as Gold, Silver, Nickel and Copper (bead or catalyst), etc.; and Nucleic Acids, such as DNA, RNA, and siRNA for any convenient gene of interest. In some cases, the cargo moieties are anthracycline chemotherapeutic compounds, such as doxorubicin (DOX).

Any of a number of drugs are suitable for use as a cargo moiety, or can be modified to be rendered suitable for use in the subject compounds. Drugs of interest include, but are not limited to, small molecule drugs,peptide drugs, protein drugs, enzyme drugs, metal drugs, metal catalyst drugs, and various nucleic acid based drugs.

"Small molecule drug" as used herein refers to a compound, e.g., an organic compound, naturally occurring or non-naturally occurring, which exhibits a pharmaceutical activity of interest and which is generally of a molecular weight of 800 Da or less, or 2000 Da or less, but can encompass molecules of up to 5 kDa and can be as large as 10 kDa. A small inorganic molecule refers to a molecule containing no carbon atoms, while a small organic molecule refers to a compound containing at least one carbon atom. "Peptide drug" as used herein refers to amino-acid containing polymeric compounds, and is meant to encompass naturally-occurring and non-naturally-occurring peptides, oligopeptides, cyclic peptides, polypeptides, and proteins, as well as peptide mimetics. The peptide drugs may be obtained by chemical synthesis or be produced from a genetically encoded source (e.g., recombinant source). Peptide drugs can range in molecular weight, and can be from 200 Da to 10 kDa or greater in molecular weight.

In some cases, the drug is a cancer chemotherapeutic agent. Cancer chemotherapeutic agents include non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones. Peptidic compounds can also be used. Suitable cancer chemotherapeutic agents include dolastatin and active analogs and derivatives thereof; and auristatin and active analogs and derivatives thereof (e.g., Monomethyl auristatin D (MMAD), monomethyl auristatin E (MMAE), monomethyl auristatin F (MMAF), and the like). See, e.g., WO 96/33212, WO 96/14856, and U.S. Pat. No. 6,323,315. Suitable cancer chemotherapeutic agents also include maytansinoids and active analogs and derivatives thereof (see, e.g., EP 1391213; and Liu et al (1996) Proc. Natl. Acad. Sci. USA 93:8618-8623); duocarmycins and active analogs and derivatives thereof (e.g., including the synthetic analogues, KW-2189 and CB 1-TM1); and benzodiazepines and active analogs and derivatives thereof (e.g., pyrrolobenzodiazepine (PBD).

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include, but are not limited to, folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., *vinca* alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; aziridinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation; therefore compounds that bind to the estrogen receptor are used to block this activity. Corticosteroids may inhibit T cell proliferation.

Other suitable chemotherapeutic agents include, but are not limited to, metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include, but are not limited to, immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylam ino)-7-methoxy-6-(3-(4-morpholinyl)propoxy)quinazoline); etc.

Taxanes are suitable for use. "Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose). Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

The terms "nucleic acid molecule", "oligonucleotide" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), small interfering RNA (siRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

A "therapeutically effective amount" or "efficacious amount" means the amount of a compound that, when administered to a mammal or other subject for treating a disease, condition, or disorder, is sufficient to effect such treatment for the disease, condition, or disorder. The "therapeutically effective amount" will vary depending on the compound, the disease and its severity and the age, weight, etc., of the subject to be treated.

The term "unit dosage form," as used herein, refers to physically discrete units suitable as unitary dosages for human and animal subjects, each unit containing a predetermined quantity of a compound (e.g., an aminopyrimidine compound, as described herein) calculated in an amount sufficient to produce the desired effect in association with a pharmaceutically acceptable diluent, carrier or vehicle. The specifications for unit dosage forms depend on the particular compound employed and the effect to be achieved, and the pharmacodynamics associated with each compound in the host.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal, intramuscular, subcutaneous, and the like.

Multidrug Resistant Cancer.

As used herein, the term "multidrug resistant", or "MDR" cancer refers to cancer cells that intrinsically or by acquired means are resistant to multiple classes of chemotherapeutic agents. A number of tumors overexpress the MDR-1 gene; including neuroblastoma, rhabdomyosarcoma, myeloma, non-Hodgkin's lymphomas, colon carcinoma, ovarian, breast carcinoma and renal cell cancer. Several tumor types with high MDR-1 expression derive from tissues that have a high expression of the gene, e.g. colonic epithelium. As a non-limiting example, such cells may be resistant to the spectrum of agents including: paclitaxel, doxorubicin, daunorubicin, mitoxantrone, actinomycin D, plicamycin, vincristine, vinblastine, colchicine, etoposide, teniposide, camptothecin and derivatives of thereof. By resistant, it is intended that the $IC_{50}$ (the half maximal (50%) inhibitory concentration) of the drug with respect to the cell is increased at least about 5-fold, a least about 10-fold, at least about 20-fold, or more relative to a non-resistant cell from the same type of cancer.

In some embodiments, the MDR cancer cells express one or more ABC transporter proteins. Mechanisms of MDR include transporter-mediated resistance conferred by increased expression of the transmembrane glycoprotein, P-glycoprotein (Pgp), the product of the MDR1 gene and a related membrane glycoprotein, the multidrug resistance protein (MRP1). The mrp1 gene encodes a 190-kilodalton (kDa) transmembrane protein, whose structure is strikingly homologous to P-glycoprotein/MDR1 and other members of the ATP-binding cassette (ABC) transmembrane transporter proteins. There are at least five other human MRP isoforms identified. Among them, MRP2 (cMOAT) and MRP3 are also capable of supporting efflux detoxification of cancer drugs, including epipodophyllotoxins (MRP2 and 3), doxorubicin, and cisplatin (MRP2). MRP1, MRP2, MRP3 and MRP4 can all act as methotrexate efflux pumps and can confer resistance to methotrexate. Expression of these transporters can confer resistance to an overlapping array of structurally and functionally unrelated chemotherapeutic agents, toxic xenobiotics and natural product drugs. Cells in culture exhibiting MDR generally show reduced net drug accumulation and altered intracellular drug distribution. The sequence of P-glycoprotein may be obtained as Genbank accession number NM_000927 (Chen et al. (1986) Cell 47:381-389.

In some embodiments of the invention, the cancer is assessed for its MDR status prior to treatment. Various methods are known in the art for determining whether a cell expressed an MDR transporter. In some such methods, the expression of an MDR gene is determined by quantitating the level of mRNA encoding the transporter by PCR, blot or array hybridization, in situ hybridization, and the like, as known in the art. In other embodiments, the presence of the transporter protein is directly determined, e.g. by immunoassays such as RIA, ELISA, immunohistochemistry, and the like.

In MDR1-expressing cells a decreased uptake of cytotoxic drugs can be visualized by measuring the cellular accumulation or uptake of fluorescent compounds, e.g., anthracyclines (Herweijer et al. (1989) *Cytometry* 10:463-468), verapamil-derivatives (Lelong et al. (1991) *Mol. Pharmacol.* 40:490-494), rhodamine 123 (Neyfakh (1988) Exp. Cell Res. 174:168-174); and Fluo-3 (Wall et al. (1993) *Eur. J. Cancer* 29:1024-1027). Alternatively, the sample of cells may be exposed to a calcein compound; measuring the amount of calcein compound accumulating in the specimen cells relative to control cells. Reduced calcein accumulation in specimen cells relative to control cells indicates the presence of multi-drug resistance in the biological specimen.

It will be understood by one of skill in the art that P-glycoprotein-associated MDR displays significant phenotypic heterogeneity. The relative degree of cross-resistance to drugs varies based on the cell line and the selecting drug. While the level of drug resistance is roughly correlated with the level of P-glycoprotein expression, protein and RNA levels may be disproportionately higher or lower than expected for the level of resistance observed. This phenotypic diversity may be the result of both MDR1 mutations and of posttranslational modifications of the MDR1 gene product.

P-glycoprotein RNA or protein has been detected in tumor specimens derived from patients with acute and chronic leukemias, ovarian cancer, multiple myeloma, breast cancer, neuroblastoma, soft tissue sarcomas, renal cell carcinoma, and others. Results have tended to link increased P-glycoprotein expression with a history of prior therapy or toxin exposure, and poorer treatment outcome. The relationship between increased P-glycoprotein and adverse outcome in human cancers is strongest in hematologic malignancies. Significant correlations between P-glycoprotein and adverse outcome in pediatric rhabdomyosarcoma and neuroblastoma have also been reported.

Cancers of interest include without limitation, carcinomas, e.g. colon, prostate, breast, melanoma, ductal, endometrial, stomach, dysplastic oral mucosa, invasive oral cancer, non-small cell lung carcinoma, transitional and squamous cell urinary carcinoma, etc.; neurological malignancies, e.g. neuroblastoma, gliomas, etc.; hematological malignancies, e.g. childhood acute leukemia, non-Hodgkin's lymphomas, and other myeloproliferative disorders, chronic lymphocytic leukemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, etc.; and the like. Cancers of interest particularly include hematologic cancers, e.g. acute myelogenous leukemia, chronic myelogenous leukemia, acute lymphocytic leukemia, Hodgkin's lymphoma, non-Hodgkin's lymphoma, multiple myeloma, etc.; ovarian cancer; breast cancer; neuroblastoma; soft tissue sarcomas; renal cell carcinoma, all of which are have a high tendency to develop multidrug resistance.

Chemotherapeutic Agent.

Agents that act to reduce cellular proliferation are known in the art and widely used. Agents of interest in the present invention include, without limitation, agents that are affected by transporter-mediated multidrug resistance. Such agents may include *vinca* alkyloids, taxanes, epipodophyllotoxins, anthracyclines, actinomycin, etc.

Anthracyclines are a class of chemotherapeutic agents based upon samine and tetra-hydro-naphthacene-dione. These compounds are used to treat a wide range of cancers, including (but not limited to) leukemias, lymphomas, and breast, uterine, ovarian, and lung cancers. Useful agents include daunorubicin hydrochloride (daunomycin, rubidomycin, cerubidine), doxorubicin, epirubicin, idarubicin, and mitoxantrone.

*Vinca* alkyloids are a class of drugs originally derived from the *Vinca* plant, and include vinblastine, vincristine, vindesine, vinorelbine. These agents bind tubulin, thereby inhibiting the assembly of microtubules.

Taxanes are diterpenes produced by the plants of the genus *Taxus*, and derivatives thereof. The principal mechanism of the taxane class of drugs is the disruption of microtubule function. It does this by stabilizing GDP-bound tubulin in the microtubule. The class includes paclitaxel and docetaxel.

Epipodophyllotoxins are naturally occurring alkaloids, and derivatives thereof. Epipodophyllotoxin derivatives currently used in the treatment of cancer include etoposide, teniposide.

Quinoline alkaloids are another class of interest. This class includes camptothecin, SN-38, DX-8951f, topotecan, 9-aminocamptothecin, BN 80915, irinotecan, DB 67, BNP 1350, exatecan, lurtotecan, ST 1481, and CKD 602.

Other natural products include azathioprine; brequinar; phenoxizone biscyclopeptides, e.g. dactinomycin; basic glycopeptides, e.g. bleomycin; anthraquinone glycosides, e.g. plicamycin (mithrmycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other chemotherapeutic agents include metal complexes, e.g. cisplatin (cis-DDP), carboplatin, etc.; ureas, e.g. hydroxyurea; and hydrazines, e.g. N-methylhydrazine. Retinoids, e.g. vitamin A, 13-cis-retinoic acid, trans-retinoic acid, isotretinoin, etc.; carotenoids, e.g. beta-carotene, vitamin D, etc. Retinoids regulate epithelial cell differentiation and proliferation, and are used in both treatment and prophylaxis of epithelial hyperproliferative disorders.

The chemotherapeutic drug can be linked to the guanidinium-rich oligophosphoester according to a number of embodiments. The agent is generally not attached to any of the guanidinium sidechains so that they are free to interact with the target membrane. The conjugates of the invention can be prepared by straightforward synthetic schemes. Furthermore, the conjugate products are usually substantially homogeneous in length and composition, so that they provide greater consistency and reproducibility in their effects than heterogeneous mixtures.

Suitable linkers are known in the art (see, for example, Wong, S. S., Ed., Chemistry of Protein Conjugation and Cross-Linking, CRC Press, Inc., Boca Raton, Fla. (1991). In particular, carbamate, ester, thioether, disulfide, and hydrazone linkages are generally easy to form and suitable for most applications. Other linkers such as trimethyl lock (see Wang et. al. J. Org. Chem., 62:1363(1997) and Chandran et al., J. Am. Chem. Soc., 127:1652 (2005)), quinine methide linker (see Greenwald et. al. J. Med. Chem., 42:3657 (1999) and Greenwald et. al. Bioconjugate Chem., 14:395 (2003)), diketopiperazine linker and derivatives of thereof are also of interest of this invention.

Ester and disulfide linkages are preferred if the linkage is to be readily degraded in a biological environment, after transport of the substance across the cell membrane. Ester linkers can also be cleaved extracellularly with the help of extracellular esterases. Various functional groups (hydroxyl, amino, halogen, thiol etc.) can be used to attach the chemotherapeutic drug to the transport polymer or to a linker, incorporated between a drug and a transporter. Groups which are not known to be part of an active site of the biologically active agent are preferred, particularly if the polypeptide or any portion thereof is to remain attached to the substance after delivery. Releasable linkers could be used if the attachment is done at the site of molecule important for biological activity.

To help minimize side-reactions, guanidinium moieties can be blocked using conventional protecting groups, such as carbobenzyloxy groups (CBZ), di-t-BOC, PMC, Pbf, N—$NO_2$, and the like.

Coupling reactions are performed by known coupling methods in any of an array of solvents, such as N,N-dimethyl formamide (DMF), N-methyl pyrrolidinone, dichloromethane, water, and the like. Exemplary coupling reagents include, for example, O-benzotriazolyloxy tetramethyluronium hexafluorophosphate (HATU), dicyclohexyl carbodiimide, bromo-tris(pyrrolidino) phosphonium bromide (PyBroP), etc. Other reagents can be included, such as N,N-dimethylamino pyridine (DMAP), 4-pyrrolidino pyridine, N-hydroxy succinimide, N-hydroxy benzotriazole, and the like.

The cargo may be attached to the transporter moiety using a linkage that is specifically cleavable or releasable. The use of such linkages is particularly important for chemotherapeutic drugs that are inactive until the attached transporter moiety is released. In some cases, such conjugates can be referred to as prodrugs, in that the release of the delivery-enhancing transporter from the drug results in conversion of the drug from an inactive to an active form. As used herein, "cleaved" or "cleavage" of a conjugate or linker refers to release of a chemotherapeutic drugs from a transporter moiety, thereby releasing an active chemotherapeutic drugs. "Specifically cleavable" or "specifically releasable" refers to the linkage between the transporter and the drug being cleaved, rather than the transporter being degraded (e.g., by proteolytic degradation). However, this "degradable" mechanism of drug release could also be used in the invention.

In some embodiments, the linkage is a readily cleavable linkage, meaning that it is susceptible to cleavage under conditions found in vivo. Thus, upon passing into a cancer cell the drug is released from the transporter. Readily cleavable linkages can be, for example, linkages that are cleaved by an enzyme having a specific activity (e.g., an esterase, protease, phosphatase, peptidase, and the like) or by hydrolysis. For this purpose, linkers containing carboxylic acid esters and disulfide bonds are sometimes preferred, where the former groups are hydrolyzed enzymatically or chemically, and the latter are severed by disulfide exchange, e.g., in the presence of glutathione. The thiol resulting from glutathione cleavage was expected to cyclize into the proximate carbonyl group of the linker, leading subsequently to the release of free drug at a rate controlled by linker design. In some embodiments, the linkage is a non-covalent association in which the transporter and cargo are held together by one or more weak associations including electrostatic, hydrogen bonding, or dispersion forces.

As used herein, the phrase "having the formula" or "having the structure" is not intended to be limiting and is used in the same way that the term "comprising" is commonly used. The term "independently selected from" is used herein to indicate that the recited elements, e.g., R groups or the like, can be identical or different.

As used herein, the terms "may," "optional," "optionally," or "may optionally" mean that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The term "alkyl" as used herein refers to a branched or unbranched saturated hydrocarbon group (i.e., a monoradical) typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms. The term "lower alkyl" intends an alkyl group of 1 to 6 carbon atoms. "Substituted alkyl" refers to alkyl substituted with one or more substituent groups, and this includes instances wherein two hydrogen atoms from the same carbon atom in an alkyl substituent are replaced, such as in a carbonyl group (i.e., a substituted alkyl group may include a —C(═O)— moiety). The terms "heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$— alkyl, —SO$_2$-aryl, —SO$_2$-heteroaryl, and —NR$^a$R$^b$, wherein R' and R'' may be the same or different and are chosen from hydrogen, optionally substituted alkyl, cycloalkyl, alkenyl, cycloalkenyl, alkynyl, aryl, heteroaryl and heterocyclic.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 18 carbon atoms, and for example may contain 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "C$_1$-C$_6$ alkoxy" or "lower alkoxy" herein may, for example, may contain 1 to 3 carbon atoms, and as a further example, such substituents may contain 1 or 2 carbon atoms (i.e., methoxy and ethoxy).

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—

"Acylamino" refers to the groups —NR$^{20}$C(O)alkyl, —NR$^{20}$C(O)substituted alkyl, N R$^{20}$C(O)cycloalkyl, —NR$^{20}$C(O)substituted cycloalkyl, —NR$^{20}$C(O)cycloalkenyl, —NR$^{20}$C(O)substituted cycloalkenyl, —NR$^{20}$C(O) alkenyl, —NR$^{20}$C(O)substituted alkenyl, —NR$^{20}$C(O)alkynyl, —NR$^{20}$C(O)substituted alkynyl, —NR$^{20}$C(O)aryl, —NR$^{20}$C(O)substituted aryl, —NR$^{20}$C(O)heteroaryl, —NR$^{20}$C(O)substituted heteroaryl, —NR$^{20}$C(O) heterocyclic, and —NR$^{20}$C(O)substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

The term "aryl" as used herein, and unless otherwise specified, refers to an aromatic substituent generally, although not necessarily, containing 5 to 30 carbon atoms and containing a single aromatic ring or multiple aromatic rings that are fused together, directly linked, or indirectly linked (such that the different aromatic rings are bound to a common group such as a methylene or ethylene moiety). Aryl groups may, for example, contain 5 to 20 carbon atoms, and as a further example, aryl groups may contain 5 to 12 carbon atoms. For example, aryl groups may contain one aromatic ring or two or more fused or linked aromatic rings (i.e., biaryl, aryl-substituted aryl, etc.). Examples include phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms. Aralkyl and alkaryl groups may, for example, contain 6 to 20 carbon atoms, and as a further example, such groups may contain 6 to 12 carbon atoms.

The term "alkylene" as used herein refers to a di-radical alkyl group. Unless otherwise indicated, such groups include saturated hydrocarbon chains containing from 1 to 24 carbon atoms, which may be substituted or unsubstituted, may contain one or more alicyclic groups, and may be heteroatom-containing. "Lower alkylene" refers to alkylene linkages containing from 1 to 6 carbon atoms. Examples include, methylene (—$CH_2$—), ethylene (—$CH_2CH_2$—), propylene (—$CH_2CH_2CH_2$—), 2-methylpropylene (—$CH_2$—$CH(CH_3)$—$CH_2$—), hexylene (—$(CH_2)_6$—) and the like.

Similarly, the terms "alkenylene," "alkynylene," "arylene," "aralkylene," and "alkarylene" as used herein refer to di-radical alkenyl, alkynyl, aryl, aralkyl, and alkaryl groups, respectively.

The term "amino" is used herein to refer to the group —$NZ^1Z^2$ wherein $Z^1$ and $Z^2$ are hydrogen or nonhydrogen substituents, with nonhydrogen substituents including, for example, alkyl, aryl, alkenyl, aralkyl, and substituted and/or heteroatom-containing variants thereof.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the terms "heterocyclic" or "heterocycle" refer to a cyclic substituent that is heteroatom-containing, the terms "heteroaryl" and "heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, furyl, pyrimidinyl, imidazolyl, 1,2,4-triazolyl, tetrazolyl, etc., and examples of heteroatom-containing alicyclic groups are pyrrolidino, morpholino, piperazino, piperidino, tetrahydrofuranyl, etc.

"Hydrocarbyl" refers to univalent hydrocarbyl radicals containing 1 to about 30 carbon atoms, including 1 to about 24 carbon atoms, further including 1 to about 18 carbon atoms, and further including about 1 to 12 carbon atoms, including linear, branched, cyclic, saturated and unsaturated species, such as alkyl groups, alkenyl groups, aryl groups, and the like. A hydrocarbyl may be substituted with one or more substituent groups. The term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation, functional groups, and the hydrocarbyl moieties $C_1$-$C_{24}$ alkyl (including $C_1$-$C_{18}$ alkyl, further including $C_1$-$C_{12}$ alkyl, and further including $C_1$-$C_6$ alkyl), $C_2$-$C_{24}$ alkenyl (including $C_2$-$C_{18}$ alkenyl, further including $C_2$-$C_{12}$ alkenyl, and further including $C_2$-$C_6$ alkenyl), $C_2$-$C_{24}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{30}$ aralkyl (including $C_6$-$C_{20}$ aralkyl, and further including $C_6$-$C_{12}$ aralkyl). The above-mentioned hydrocarbyl moieties may be further substituted with one or more functional groups or additional hydrocarbyl moieties such as those specifically enumerated. Unless otherwise indicated, any of the groups described herein are to be interpreted as including substituted and/or heteroatom-containing moieties, in addition to unsubstituted groups.

By the term "functional groups" is meant chemical groups such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), mono-substituted $C_1$-$C_{24}$ alkylcarbamoyl (—(CO)—NH($C_1$-$C_{24}$ alkyl)), di-substituted alkylcarbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—C≡N), isocyano (—$N^+$≡$C^-$), cyanato (—O—C≡N), isocyanato (—O—$N^+$≡C—), isothiocyanato (—S—C≡N), azido (—N=$N^+$=$N^-$), formyl (—(CO)—H), thioformyl (—(CS)—H), amino (—$NH_2$), mono- and di-(C1-C24 alkyl)-substituted amino, mono- and di-($C_5$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R=hydrogen, $C_1$-$C_{24}$ alkyl, $C_5$-$C_2O$ aryl, $C_6$-$C_{20}$ alkaryl, $C_6$-$C_{20}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—$NO_2$), nitroso (—NO), sulfo (—$SO_2$—OH), sulfonato (—$SO_2$—O—), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)(O—)$_2$), phosphinato (—P(O)(O—)$_2$), phospho (—$PO_2$), and phosphino (—$PH_2$), mono- and di-($C_1$-$C_{24}$ alkyl)-substituted phosphino, mono- and di-($C_5$-$C_{20}$ aryl)-substituted phosphine. In addition, the aforementioned functional groups may, if a particular group permits, be further substituted with one or more additional functional groups or with one or more hydrocarbyl moieties such as those specifically enumerated above.

In addition to the groups disclosed with respect to the individual terms herein, substituent groups for substituting for one or more hydrogens (any two hydrogens on a single carbon can be replaced with =O, =N$R^{70}$, =N—O$R^{70}$, =$N_2$ or =S) on saturated carbon atoms in the specified group or radical are, unless otherwise specified, —$R^{60}$, halo, =O, —O$R^{70}$, —S$R^{70}$, —N$R^{80}R^{80}$, trihalomethyl, —CN, —OCN, —SCN, —NO, —$NO_2$, =$N_2$, —$N_3$, —$SO_2R^{70}$, —$SO_2$O$^-$M$^+$, —$SO_2$O$R^{70}$, —$OSO_2R^{70}$, —$OSO_2$O$^-$M$^+$, —$OSO_2$O$R^{70}$, —P(O)(O$^-$)$_2$(M$^+$)$_2$, —P(O)(O$R^{70}$)O$^-$M$^+$, —P(O)(O$R^{70}$)$_2$, —C(O)$R^{70}$, —C(S)$R^{70}$, —C(N$R^{70}$)$R^{70}$, —C(O)O$^-$M$^+$, —C(O)O$R^{70}$, —C(S)O$R^{70}$, —C(O)N$R^{80}R^{80}$, —C(N$R^{70}$)N$R^{80}R^{80}$, —OC(O)$R^{70}$, —OC(S)$R^{70}$, —OC(O) O$^-$M$^+$, —OC(O)O$R^{70}$, —OC(S)O$R^{70}$, —N$R^{70}$C(O)$R^{70}$, —N$R^{70}$C(S)$R^{70}$, —N$R^{70}$C$O_2^-$M$^+$, —N$R^{70}$C$O_2R^{70}$, —N$R^{70}$C(S)O$R^{70}$, —N$R^{70}$C(O)N$R^{80}R^{80}$, —N$R^{70}$C(N$R^{70}$)$R^{70}$ and —N$R^{70}$C(N$R^{70}$)N$R^{80}R^{80}$, where $R^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N($R^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —N$R^{80}R^{80}$ is meant to include —$NH_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —$R^{60}$, halo, —O$^-$M$^+$, —O$R^{70}$, —S$R^{70}$, —S$^-$M$^+$, —N$R^{80}R^{80}$, trihalomethyl, —$CF_3$, —CN, —OCN, —SCN, —NO, —$NO_2$, —$N_3$, —$SO_2R^{70}$, —$SO_3^-$M$^+$, —$SO_3R^{70}$, —$OSO_2R^{70}$, —$OSO_3^-$M$^+$, —$SO_3R^{70}$, —$PO_3^{-2}$(M$^+$)$_2$, —P(O)(O$R^{70}$)O$^-$M$^+$, —P(O)(O$R^{70}$)$_2$, —O(O)$R^{70}$, —O(S)$R^{70}$, —C(N$R^{70}$)$R^{70}$, —$CO_2^-$M$^+$, —$COO_2R^{70}$, —C(S)O$R^{70}$, —C(O)N$R^{80}R^{80}$, —C(N$R^{70}$)N$R^{80}R^{80}$, —OC(O)$R^{70}$, —OC(S)$R^{70}$, —$OCO_2^-$M$^+$, —$OCO_2R^{70}$, —OC(S)O$R^{70}$, —N$R^{70}$C(O)$R^{70}$, —N$R^{70}$C(S)$R^{70}$, —N$R^{70}$C$O_2^-$M$^+$, —N$R^{70}$C$O_2R^{70}$, —N$R^{70}$C(S)O$R^{70}$, —N$R^{70}$C(O)N$R^{80}R^{80}$, —N$R^{70}$C(N$R^{70}$)$R^{70}$ and —N$R^{70}$C(N$R^{70}$)N$R^{80}R^{80}$, where $R^{60}$, $R^{70}$, $R^{80}$ and M$^+$ are as previously defined, provided that in case of substituted alkene or alkyne, the substituents are not —O$^-$M$^+$, —O$R^{70}$, —S$R^{70}$, or —S$^-$M$^+$.

In addition to the groups disclosed with respect to the individual terms herein, substituent groups for hydrogens on nitrogen atoms in "substituted" heteroalkyl and cycloheteroalkyl groups are, unless otherwise specified, —$R^{60}$, —O$^-$M$^+$, —O$R^{70}$, —S$R^{70}$, —S$^-$M$^+$, —N$R^{80}R^{80}$, trihalomethyl, —$CF_3$, —CN, —NO, —$NO_2$, —S(O)$_2R^{70}$, —S(O)$_2$O$^-$M$^+$, —S(O)$_2$O$R^{70}$, —OS(O)$_2R^{70}$, —OS(O)$_2$O$^-$M$^+$, —OS(O)$_2$O$R^{70}$, —P(O)(O$^-$)$_2$(M$^+$)$_2$, —P(O)(O$R^{70}$)O$^-$M$^+$, —P(O)(O$R^{70}$)(O$R^{70}$), —C(O)$R^{70}$, —C(S) $R^{70}$, —C(N$R^{70}$)$R^{70}$, —C(O)O$R^{70}$, —C(S)O$R^{70}$, —C(O)N$R^{80}R^{80}$, —C(N$R^{70}$)N$R^{80}R^{80}$, —OC(O)$R^{70}$, —OC(S)$R^{70}$, —OC(O)O$R^{70}$, —OC(S)O$R^{70}$, —N$R^{70}$C(O)$R^{70}$, —N$R^{70}$C(S)$R^{70}$, —N$R^{70}$C(O)O$R^{70}$, —N$R^{70}$C(S)O$R^{70}$, —N$R^{70}$C(O)N$R^{80}R^{80}$, —N$R^{70}$C(N$R^{70}$)$R^{70}$ and —N$R^{70}$C(N$R^{70}$)N$R^{80}R^{80}$, where $R^{60}$, $R^{70}$, $R^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

By "linking" or "linker" as in "linking group," "linker moiety," etc., is meant a bivalent moiety that connects two groups via covalent or non-covalent bonds. As used herein, the term "linker" or "linkage" refers to a linking moiety that connects two groups and has a backbone of 200 atoms or less in length. A linker or linkage may be a covalent bond that connects two groups or a chain of between 1 and 200 atoms in length, for example of about 1, 2, 3, 4, 5, 6, 8, 10, 12, 14, 16, 18 or 20 atoms in length, such as a linker of 10 or more atoms in length, 20 atoms or more, 30 atoms or more, 40 atoms or more, 50 atoms or more in length, 100 atoms or more in length. The linker may be linear, branched, cyclic or a single atom. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example with an alkyl, aryl or alkenyl group. A linker may include, without limitations, oligo(ethylene glycol), PEG or modified PEG linkers, peptidic linkers, ethers, thioethers, tertiary amines, alkyls, which may be straight or branched, e.g., methyl, ethyl, n-propyl, 1-methylethyl (iso-propyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

As used herein, the term "cleavable linker" refers to a linker that can be selectively cleaved to produce two products. Application of suitable cleavage conditions to a molecule containing a cleavable linker that is cleaved by the cleavage conditions will produce two byproducts. A cleavable linker of the present invention is stable, e.g. to physiological conditions, until it is contacted with a cleavage-inducing stimulus, e.g., an agent such as an enzyme or other cleavage-inducing agent such as chemical agent, light, etc. Exemplary conditions are set forth below.

Examples of such linking groups include alkylene, alkenylene, alkynylene, arylene, alkarylene, aralkylene, and linking moieties containing functional groups including, without limitation: amido (—NH—CO—), ureylene (—NH—CO—NH—), imide (—CO—NH—CO—), epoxy (—O—), epithio (—S—), epidioxy (—O—O—), carbonyldioxy (—O—CO—O—), alkyldioxy (—O—(CH2)n-O—), epoxyimino (—O—NH—), epimino (—NH—), carbonyl (—CO—), etc. Any convenient orientation and/or connections of the linkers to the linked groups may be used. In certain embodiments, the linker (L) includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol. Linkers of interest include, but are not limited to, units of polymers such as polyethylene glycols, polyethylenes and polyacrylates, amino acid residue(s), carbohydrate-based polymers or carbohydrate residues and derivatives thereof, polynucleotides, alkyl groups, aryl groups, heterocycle groups, cleavable linker groups, combinations thereof, and substituted versions thereof.

In some embodiments, the linker includes a cleavable moiety (e.g., a chemically cleavable moiety, an enzymatically cleavable moiety (such as, but not limited to, a protease cleavable moiety, a glucuronidase cleavable moiety, a beta-lactamase cleavable moiety, etc.), a photocleavable moiety, and the like. In certain embodiments, the cleavable moiety is a para-amino-benzyloxycarbonyl group, a meta-amino-benzyloxycarbonyl group, a para-amino-benzyloxy group, a meta-amino-benzyloxy group, para-aminobenzyl, an acetal group, a disulfide, a hydrazine, a protease-cleavable moiety, a glucuronidase cleavable moiety, a beta-lactamase cleavable moiety, or an ester.

When the term "substituted" appears prior to a list of possible substituted groups, it is intended that the term apply to every member of that group. For example, the phrase "substituted alkyl and aryl" is to be interpreted as "substituted alkyl and substituted aryl."

In certain embodiments, a substituent may contribute to optical isomerism and/or stereo isomerism of a compound. Salts, solvates, hydrates, and prodrug forms of a compound are also of interest. All such forms are embraced by the present disclosure. Thus the compounds described herein include salts, solvates, hydrates, prodrug and isomer forms thereof, including the pharmaceutically acceptable salts, solvates, hydrates, prodrugs and isomers thereof. In certain embodiments, a compound may be a metabolized into a pharmaceutically active derivative.

Unless otherwise specified, reference to an atom is meant to include isotopes of that atom. For example, reference to H is meant to include 1H, 2H (i.e., D) and 3H (i.e., T), and reference to C is meant to include 12C and all isotopes of carbon (such as 13C).

Definitions of other terms and concepts appear throughout the detailed description below.

DETAILED DESCRIPTION OF THE EMBODIMENTS

Guanidinium-rich oligophosphotriester transporter compounds and methods of making and/or using the same are provided. Also provided are pharmaceutical compositions that include the subject transporter compounds, where the transporter is usually joined to a cargo moiety of interest, and is formulated with a pharmaceutically acceptable excipient.

Formulations may be provided in a unit dose, where the dose provides an amount of the compound effective to afford a therapeutic effect.

Transporter compounds of the present disclosure may have a formula (I) as follows:

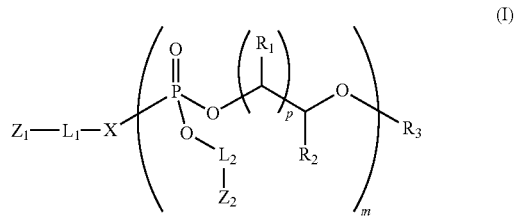

where $Z_1$ is a cargo moiety (e.g., as described herein), a reactive functional group or a protected functional group;

$L_1$ is an optional linker;

X is O, S, NH or $CH_2$;

each $L_2$ is a linker;

each $Z_2$ is a guanidine group or a protected guanidine group;

$R_3$ is H, an alkyl, a substituted alkyl, an acyl, a substituted acyl, an aryl, a substituted aryl, a heteroaryl or a substituted heteroaryl;

each $R_1$ and $R_2$ are independently H, an alkyl or a substituted alkyl;

each p is independently 1, 2 or 3; and m is 50 or less.

In some embodiments of formula (I), $Z_1$ is a cargo moiety. In some embodiments of formula (I), $Z_1$ is a reactive functional group. In some embodiments of formula (I), $Z_1$ is a protected functional group. Any convenient reactive functional groups, and protected versions thereof can be utilized in the subject compounds. In some cases, the reactive functional group is a chemoselective functional group. Chemoselective functional groups of interest include, but are not limited to, two thiol groups, thiols and maleimide or iodoacetamide, as well as groups that can react with one another via Click chemistry, e.g., azide and alkyne groups (e.g., cyclooctyne groups). Chemoselective functional groups of interest, include, but are not limited to, thiols, alkyne, a cyclooctyne, an azide, a phosphine, a maleimide, an alkoxyamine, an aldehyde and protected versions thereof, and percursors thereof. In certain embodiments, the chemoselective functional group is a thiol. In certain embodiments, the chemoselective functional group is a protected thiol, such as a dithiopyridyl protected thiol.

In some embodiments of formula (I), $L_1$ is absent. In some embodiments of formula (I), $L_1$ is a linker. In certain instances $L_1$ is a cleavable linker. In certain instances $L_1$ is a non-cleavable linker. As used herein, the term "cleavable linker" refers to a linker that can be selectively cleaved to produce two products. Application of suitable cleavage conditions to a molecule containing a cleavable linker that is cleaved by the cleavage conditions will produce two byproducts. A cleavable linker of the present disclosure is stable, e.g. to physiological conditions, until it is contacted with a cleavage-inducing stimulus, e.g., an agent such as an enzyme or other cleavage-inducing agent such as chemical agent, light, etc.

In some instances, the linker $L_1$ is a C1-C20 linker, such as an substituted or unsubstituted C1-C20 alkyl linker. In certain embodiments, the linker includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol. Linkers of interest include, but are not limited to, units of polymers such as polyethylene glycols, polyethylenes and polyacrylates, amino acid residue(s), carbohydrate-based polymers or carbohydrate residues and derivatives thereof, polynucleotides, alkyl groups, aryl groups, heterocycle groups, cleavable linker groups, combinations thereof, and substituted versions thereof.

In some embodiments, the linker includes a cleavable moiety (e.g., a chemically cleavable moiety, an enzymatically cleavable moiety (such as, but not limited to, a protease cleavable moiety, a glucuronidase cleavable moiety, a beta-lactamase cleavable moiety, etc.), a photocleavable moiety, and the like. In certain embodiments, the cleavable moiety is a para-amino-benzyloxycarbonyl group, a meta-amino-benzyloxycarbonyl group, a para-amino-benzyloxy group, a meta-amino-benzyloxy group, para-aminobenzyl, an acetal group, a disulfide, a hydrazine, a protease-cleavable moiety, a glucuronidase cleavable moiety, a beta-lactamase cleavable moiety, or an ester.

In some embodiments of formula (I), X is O, S or NH. In some embodiments of formula (I), X is O. In some embodiments of formula (I), X is S. In some embodiments of formula (I), X is NH. In some embodiments of formula (I), X is derived from a C-nucleophile, e.g., X is $CH_2$.

In some embodiments of formula (I), $L_2$ is a non-cleavable linker, e.g., a non-cleavable linker as described herein. In some embodiments of formula (I), $L_2$ is a C1-C20 linker, such as an substituted or unsubstituted C1-C20 alkyl linker. In some embodiments of formula (I), $L_2$ is a substituted or unsubstituted C2-C10 alkyl linker. In some embodiments of formula (I), $L_2$ is —$(CH_2)_n$—, where n is 1 to 20, such as 2 to 10, such as 2, 3, 4, 5, 6, 7, 8, 9 or 10.

The guanidine groups of the subject compounds can be protected or masked (e.g., during synthesis) and then deprotected or unmasked according to any convenient strategy. In some embodiments of formula (I), $Z_2$ is an guanidine group (e.g., —NHC(=NH)—$NH_2$ or —NHC(=$NH_2$+)—$NH_2$). It is understood that the guanidine group can be charged or uncharged depending on the local environment, e.g., physiological aqueous conditions around or inside a cell. In some embodiments of formula (I), $Z_2$ is a protected guanidine group (e.g., —NHC(=$NZ_3$)—$NHZ_3$, where each $Z_3$ is a guanidine protecting group, such as a Boc protecting group.

In some embodiments of formula (I), $R_3$ is H. In some embodiments of formula (I), $R_3$ is alkyl. In some embodiments of formula (I), $R_3$ is an acyl, such as $R_4CO$— where $R_4$ is an alkyl or a substituted alkyl.

Any convenient $R_3$ terminal group can be installed after oligomerization using a variety of chemistries. In some embodiments of formula (I), $R_1$ and $R_2$ are each H. In some embodiments of formula (I), p is 1. In some embodiments of formula (I), p is 2. In some embodiments of formula (I), p is 3.

In some embodiments of formula (I), m is 2 or more, such as 3 or more, 4 or more, 5 or more, 6 or more, 7 or more, 8 or more, 9 or more, or 10 or more. In some embodiments of formula (I), m is 40 or less, such as 35 or less, 30 or less, 25 or less, 20 or less, 15 or less, or even less. In some embodiments of formula (I), m is 2 to 50, such as 3 to 40, 4 to 30, 5 to 30, 6 to 30 or 8 to 30. In some embodiments of formula (I), m is about 8 to about 20. In some embodiments of formula (I), the compound is about 8 to about 20 units in length. In certain instances, m represents an average length of the oligomeric molecule, where m is in the range of 2 to 50, such as 3 to 40, 4 to 30, 5 to 30, 6 to 30 or 8 to 30. In some embodiments of formula (I), m represents an average length in the range of about 8 to about 20.

In some embodiments of formula (I), the compound has formula (II):

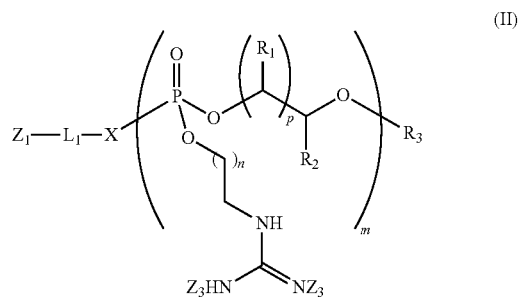

(II)

where n is 1 to 30 (e.g., 4 to 25) and each $Z_3$ is H or a protecting group. In some embodiments of formula (II), each $Z_3$ is H. In some embodiments of formula (II), each $Z_3$ is an acid labile protecting group. In some embodiments of formula (II), each $Z_3$ is a carbamate protecting group, such as a Boc, Cbz or Fmoc protecting group.

In some embodiments of formula (I), the compound has formula (III):

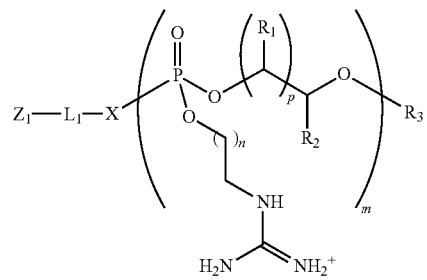

where n is 1 to 30.

In some embodiments of formula (III), each $R_1$ and $R_2$ are each H, such that the compound has formula (IV):

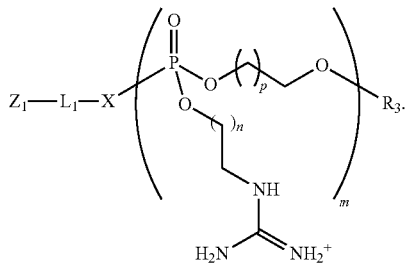

(IV)

In some embodiments of formula (IV), p is 2, such that the compound has formula (V):

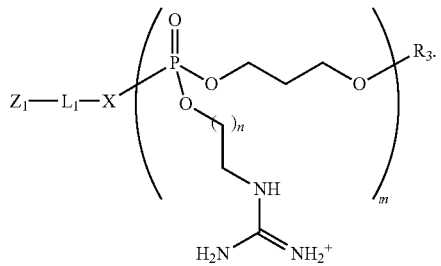

(V)

In some embodiments of formula (IV), p is 1, such that the compound has formula (VI):

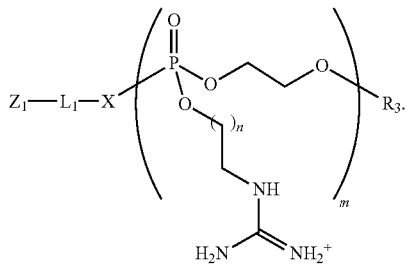

(VI)

In some embodiments of formulae (II)-(VI), $Z_1$ is a cargo moiety. In some embodiments of formulae (II)-(VI), $Z_1$ is a reactive functional group, e.g., a chemoselective functional group. In some embodiments of formulae (II)-(VI), $Z_1$ is a protected functional group.

In some embodiments of formulae (II)-(VI), $L_1$ is absent. In some embodiments of formulae (II)-(VI), $L_1$ is a linker. In certain instances of formulae (II)-(VI), $L_1$ is a cleavable linker. In certain instances of formulae (II)-(VI), $L_1$ is a non-cleavable linker.

In some instances of formulae (II)-(VI), the linker $L_1$ is a C1-C20 linker, such as an substituted or unsubstituted C1-C20 alkyl linker. In certain embodiments of formulae (II)-(VI), the linker $L_1$ includes a polymer.

In some embodiments of formula (I), X is O, S or NH. In some embodiments of formulae (III)-(VI), X is O. In some embodiments of formulae (II)-(VI), X is S. In some embodiments of formulae (II)-(VI), X is NH. In some embodiments of formula (I), X is derived from a C-nucleophile, e.g., X is $CH_2$.

In some embodiments of formulae (II)-(VI), n is 1 to 20, such as 2 to 10, such as 2, 3, 4, 5, 6, 7, 8, 9 or 10.

In some embodiments of formulae (II)-(VI), $R_3$ is H. In some embodiments of formulae (II)-(VI), $R_3$ is alkyl. In some embodiments of formulae (II)-(VI), $R_3$ is an acyl, such as $R_4CO$— where $R_4$ is an alkyl or a substituted alkyl.

In some embodiments of formulae (II)-(VI), m is 2 or more, such as 3 or more, 4 or more, 5 or more, 6 or more, 7 or more, 8 or more, 9 or more, or 10 or more. In some embodiments of formulae (II)-(VI), m is 40 or less, such as 35 or less, 30 or less, 25 or less, 20 or less, 15 or less, or even less. In some embodiments of formulae (II)-(VI), m is 2 to 50, such as 3 to 40, 4 to 30, 5 to 30, 6 to 30 or 8 to 30. In some embodiments of formulae (II)-(VI), m is about 8 to about 20. In some embodiments of formulae (II)-(VI), the compound is about 8 to about 20 units in length. In certain instances of formulae (II)-(VI), m represents an average length of the oligomeric molecule, where m is in the range of 2 to 50, such as 3 to 40, 4 to 30, 5 to 30, 6 to 30 or 8 to 30. In some embodiments of formulae (II)-(VI), m represents an average length in the range of about 8 to about 20.

In some embodiments, the subject compound includes formula (VII):

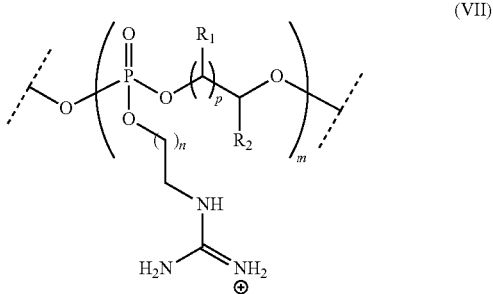

(VII)

where $R_1$, $R_2$, n, m and p are as defined for formula (I)-(VI). In certain instances of formula (VII), n is from about 4 to about 25 units in length; m is from about 8 to about 20 units in length; p is from 1 to about 3 units in length; and $R_1$ and $R_2$ are independently H, alkyl and substituted alkyl.

Pharmaceutical Compositions

The herein-discussed transporters can be formulated using any convenient excipients, reagents and methods. Compositions are provided in formulation with a pharmaceutically acceptable excipient(s). A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7th ed., Lippincott, Williams, & Wilkins; and Handbook of Pharmaceutical Excipients (2000) A. H. Kibbe et al., eds., 3rd ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, the transporters are formulated in an aqueous buffer. Suitable aqueous buffers include, but are not limited to, acetate, succinate, citrate, and phosphate buffers varying in strengths from 5 mM to 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the formulations may further include a preservative. Suitable preservatives include, but are not limited to, a benzyl alcohol, phenol, chlorobutanol, benzalkonium chloride, and the like. In some cases, the formulation is stored at about 4° C. In some cases, the formulation is stored at −20° C. Formulations may also be lyophilized, in which case they generally include cryoprotectants such as sucrose, trehalose, lactose, maltose, mannitol, and the like. Lyophilized formulations can be stored over extended periods of time, even at ambient temperatures.

In some embodiments, the transporter and cargo are administered to individuals in a formulation with a pharmaceutically acceptable excipient(s). The subject molecules, as well as additional therapeutic agents as described herein for combination therapies, can be administered orally, topically, subcutaneously, intramuscularly, parenterally, by inhalation, IV, IP or other routes. The subject complexes and additional therapeutic agents may be administered by the same route of administration or by different routes of administration. The therapeutic agents can be administered by any suitable means including, but not limited to, for example, oral, rectal, nasal, topical (including transdermal, aerosol, buccal and sublingual), ocular, vaginal, parenteral (including subcutaneous, intramuscular, intravenous and intradermal), intravesical or injection into an affected organ.

The subject transporters may be administered in a unit dosage form and may be prepared by any methods well known in the art. Such methods include combining the subject compound with a pharmaceutically acceptable carrier or diluent which constitutes one or more accessory ingredients. A pharmaceutically acceptable carrier is selected on the basis of the chosen route of administration and standard pharmaceutical practice. Each carrier must be "pharmaceutically acceptable" in the sense of being compatible with the other ingredients of the formulation and not injurious to the subject. This carrier can be a solid or liquid and the type is generally chosen based on the type of administration being used.

Examples of suitable solid carriers include lactose, sucrose, gelatin, agar and bulk powders. Examples of suitable liquid carriers include water, pharmaceutically acceptable fats and oils, alcohols or other organic solvents, including esters, emulsions, syrups or elixirs, suspensions, solutions and/or suspensions, and solution and or suspensions reconstituted from non-effervescent granules and effervescent preparations reconstituted from effervescent granules. Such liquid carriers may contain, for example, suitable solvents, preservatives, emulsifying agents, suspending agents, diluents, sweeteners, thickeners, and melting agents. Preferred carriers are edible oils, for example, corn or canola oils. Polyethylene glycols, e.g. PEG, are also good carriers.

Any drug delivery device or system that provides for the dosing regimen of the instant disclosure can be used. A wide variety of delivery devices and systems are known to those skilled in the art.

A therapeutically effective amount of a compound in this context can be regarded as an amount that is effective in reducing the incidence (e.g., the likelihood that an individual will develop) of a disorder by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to an untreated individual, or to a placebo-treated individual.

Methods of Preparation

Any convenient methods can be utilized in preparation of the subject transporter compounds. In some cases, the subject transporter compounds can be synthesized in two steps, irrespective of oligomer length, by the organocatalytic ring-opening polymerization (OROP) of cyclic phospholane monomers, preferably 5-membered cyclic monomers, followed by optional oligomer deprotection. Initiation of oligomerization with a nucleophilic probe, where the nucleophilic atom could, for example, be a carbon, nitrogen, sulfur, or oxygen, produces upon deprotection a transporter-probe conjugate that is shown to readily enter multiple cell lines in a dose-dependent manner. Any convenient initiator compounds that are capable of ring opening of the cyclic phospholane monomer can be utilized. In general terms, the initiator compound includes a nucleophilic group that ring opens the cyclic phospholane monomer. The initiator may further include a cargo moiety (e.g., as described herein). In certain instances, the initiator includes a reactive functional group or a masked or protected functional group to which a cargo moiety of interest can be subsequently conjugated. A masked functional group is a functional group that can be easily converted from an inert form into a different reactive form, e.g., via a chemical or enzymatic reaction, or application of a stimulus, such as light.

The cyclic phospholane monomer can be selected to provide for a particular arrangement of backbone and side-chain guanidine groups. In certain embodiments, the method of preparation involves OROP of a monomer of the formula (XI):

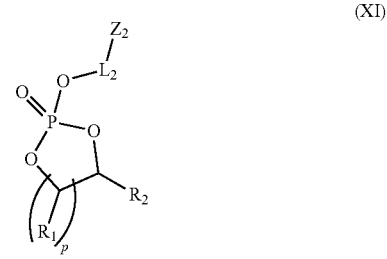

(XI)

wherein: $L_2$ is a linker; $Z_2$ is an guanidine group or a protected guanidine group; $R_1$ and $R_2$ are independently H, an alkyl or a substituted alkyl; and p is 1, 2 or 3. It is understood that any of the subject transporter compounds (e.g., as described herein, compounds of formulae (I)-(VII)) can be synthesized by adapting the subject methods to select a particular monomer of formula (XI) and a particular initiator molecule (e.g., as described herein).

In certain instances, a mixture of monomers can be utilized in the subject methods to provide a random or block co-oligomer of two or more monomeric units. It is understood that in some instances, the subject methods can arrive at a oligomeric composition that is polydisperse (e.g., includes oligomeric compounds of various lengths). In such cases, the transporter compounds may be described via and average length (e.g., as described herein).

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any purification protocol known in the art, including chromatography, such as HPLC, preparative thin layer chromatography, flash column chromatography and ion exchange chromatography. Any suitable stationary phase can be used, including normal and reversed phases as well as ionic resins. In certain embodiments, the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4th edition, Vol. 15/I, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

Exemplary synthetic methods for the subject compounds are described herein. These methods can be adapted to synthesize compounds described herein.

A method of synthesizing a compound of Claim 1, the method comprising: initiating organocatalytic ring-opening polymerization (OROP) of cyclic phospholane monomers of the formula (XI):

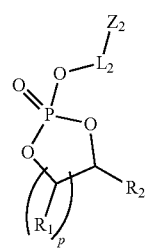

(XI)

wherein: $L_2$ is a linker; $Z_2$ is an guanidine group or a protected guanidine group; $R_1$ and $R_2$ are independently H, an alkyl or a substituted alkyl; and p is 1, 2 or 3;

with an initiator of the formula $Z_1$-$L_1$-XH (XII), wherein: $Z_1$ is a cargo moiety or a protected functional group; $L_1$ is an optional linker; and X is O, S or NH.

In certain embodiments of formula (XI), $Z_2$ is a protected guanidine group. In certain embodiments of the method, the method further comprises deprotecting $Z_2$ to produce a guanidine group.

The cargo moiety can be installed into the subject transporter compound at any convenient time, e.g., during ring-opening polymerization or after polymerization. In certain embodiments of formula (XI), $Z_1$ is a cargo moiety (e.g., as described herein). In some instances, the cargo moiety is a small molecule drug. In some instances, the cargo moiety is a chemotherapeutic agent. In certain embodiments, the formula (XII) described the cargo moiety ($Z_1$-$L_1$-XH), i.e., the cargo moiety itself includes a nucleophilic group XH suitable for initiating ring opening of the monomer.

In certain instances, $Z_1$ is a reactive functional group, or a masked or protected version thereof, such as a chemoselective functional groups. Any convenient reaction conditions and form of $Z_1$ can be selected so as not to interfere with the ring opening initiation reaction of the XH group. Chemoselective functional groups of interest which may be incorporated into an initiator for use in the subject methods, include, but are not limited to, thiols, alkyne, a cyclooctyne, an azide, a phosphine, a maleimide, an alkoxyamine, an aldehyde and protected versions thereof, and percursors thereof. In certain embodiments, the chemoselective functional group is a thiol. In certain embodiments, the chemoselective functional group is a protected thiol, such as a dithiopyridyl protected thiol.

In certain embodiments of formula (XI), $Z_1$ is a protected thiol. In certain embodiments of the method, the method further comprises deprotecting $Z_1$ to produce a reactive functional group and conjugating the reactive functional group to a cargo moiety. Any convenient conjugation chemistries and chemoselective functional group pairs can be utilized to conjugate a subject oligomeric compound to a cargo moiety of interest.

Methods of Use

Also provided are methods of using the subject transporter compounds. In some cases, the compound may find use as a generalized reservoir, e.g., for drug delivery. For example, the delivery of anthracycline chemotherapeutic compounds, such as doxorubicin (DOX). The method of use may be a method of delivering a cargo moiety (e.g., a chemotherapeutic agent) to a cell, e.g., in vitro or in vivo. In some embodiments, the method includes, contacting a cell with a subject transporter compound (e.g., as described herein), under conditions in which the cargo moiety is cleaved from the transporter compound and diffuses from the transporter compound. In some instances, the transporter compound includes a plurality of therapeutic agents.

Any convenient cargo moiety (e.g., therapeutic agents) may be delivered according to the subject methods. Therapeutic agents of interest include, but are not limited to, those convenient cargo moieties described herein. In certain instances, the therapeutic agent is a pharmaceutical agent, am imaging agent, a plasmid, a polynucleotide, a polypeptide, a chemotherapeutic agent, a pro-drug, or combination thereof. The cargo moieties may be attached to the transporter compound via a cleavable or non-cleavable linker. In certain instances, the cargo moiety remains linked to the transporter compound after delivery to the cell. In some embodiments, the cargo moieties (e.g., therapeutic agents) are cleaved under intracellular reducing conditions. In certain embodiments, the cargo moieties (e.g., therapeutic agents) are enzymatically cleaved. In some embodiments, the cargo moieties (e.g., therapeutic agents) are cleaved under intracellular pH conditions. In some embodiments, the cargo moieties (e.g., therapeutic agents) are cleaved under intracellular degradation conditions. In some embodiments, release of desired therapeutic cargo results in its activation for biological activity, e.g. pro-drug delivery. A variety of intracellular conditions of target cells may be adapted for use in the subject methods and compositions.

Any convenient configurations of transporter compound, types of linkers and modifications, and cargo moieties may be selected to provide for a desired drug release mechanisms and drug delivery, e.g., over an extended period of time. In additional embodiments, the delivered cargo can consist of an inactive pro-drug entity(ies) which becomes biologically activated upon release from the transporter compound. In further embodiments, release and activation of pro-drug cargo from the subject compounds may be dependent upon delivery to appropriate target cells, tissues, organs, etc. which contain the necessary activating agent as a means to limit pro-drug activation to desired cellular locations.

Any convenient cells can be targeted for delivery of a cargo moiety according to the subject methods. The cell may be in a biological sample. The term "sample" as used herein relates to a material or mixture of materials, typically, although not necessarily, in liquid form, containing one or more analytes of interest. In one embodiment, the term as used in its broadest sense, refers to any plant, animal or bacterial material containing cells or producing cellular metabolites, such as, for example, tissue or fluid isolated from an individual (including without limitation plasma, serum, cerebrospinal fluid, lymph, tears, saliva and tissue sections) or from in vitro cell culture constituents, as well as samples from the environment. In some cases, the sample is derived from a human. The term "sample" may also refer to a "biological sample". As used herein, the term "a biological sample" refers to a whole organism or a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). A "biological sample" can also refer to a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. In certain embodiments, the sample has been removed from an animal or plant. Biological samples of the invention include cells. The term "cells" is used in its conventional sense to refer to the basic structural unit of living organisms, both eukaryotic and prokaryotic, having at least genetic material and a cell membrane. In certain embodiments, cells include prokaryotic cells, such as from bacteria. In other embodiments, cells include eukaryotic cells, such as cells obtained from biological samples from animals, plants or fungi.

Aspects of the present disclsoure include a method of delivering a cargo moiety to a cell. In some instances, the method comprises contacting a cell with a transporter compound (e.g., as described herein) that includes the cargo moiety. The method can be performed in vitro or in vivo. The guanidinium-rich oligophosphotriester transporter compounds can provide for passage of the compounds (e.g., including the attached cargo moiety) through the cell membrane and into the cell. As such, in some cases, the method is an intracellular delivery method. In certain instances, the cargo moiety is linked to the transporter compounds via a cleavable linker (e.g., $L_1$) and the method further comprises cleaving the linker (e.g., $L_1$) to release the cargo moiety. The method of Claim 7, wherein Z1 is a chemotherapeutic drug or a dye.

In some embodiments, the cell is in vivo and the cargo moieties (e.g., therapeutic agents) are released and/or diffuse from the transporter compounds to achieve immediate, delayed, or constant therapeutic level in the cell over a suitable period of time, e.g., an extended period of time suitable for achieving a therapeutic result. Also provided are methods of treating a subject for a disease condition, the method comprising administering to the subject an effective amount of a pharmaceutical composition (e.g., as described herein) to treat a subject for the disease condition.

EXAMPLES

The following examples are put forth so as to provide those of ordinary skill in the art with a complete disclosure and description of how to make and use embodiments of the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is number average molecular weight, temperature is in degrees Centigrade, and pressure is at or near atmospheric.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present disclosure. All such modifications are intended to be within the scope of the claims appended hereto.

Example 1

Cell-Penetrating, Guanidinium-Rich Oligophosphoesters: Effective and Versatile Molecular Transporters for Drug and Probe Delivery Reported herein are a new class of molecular transporters, guanidinium-rich oligophosphoesters, which exhibit increased delivery efficacy and offer several advantages over previously explored systems (FIG. 1). In the last 15 years, synthetic polyphosphoesters have emerged as attractive biomaterials with many applications, originating with work on their synthesis and properties as synthetic DNA mimics. More recently, it has been demonstrated that nanoparticle and micellular formulations generated from polyphosphoesters can be used in drug delivery and biomedical applications.

We hypothesized that a guanidinium-functionalized phosphoester backbone would address the concerns and challenges associated with previous transporter systems. First, unlike transporters accessed by solid phase techniques in which an 8-mer requires 16 steps, the oligophosphoesters can be assembled in one step using a simple organocatalytic ring-opening polymerization (OROP). This process additionally avoids toxic metal contaminants associated with some metal-catalyzed oligomerizations. Of further importance, the resulting phosphotriester backbone imparts enhanced water-solubility over hydrophobic backbones such as poly(acrylates) or poly(lactic-co-glycolic acid). This suppresses oligomer aggregation in aqueous environments, especially after functionalization with hydrophobic linkers, side chains, or highly non-polar drugs such as paclitaxel (PTX). Additionally, oligophosphoesters have increased hydrolytic stability over other materials obtained through anionic polymerizations, specifically carbonates and esters which are generally more hydrolytically labile ($t_{1/2}$<8 hours) and thus less easily stored and used. Relative to carbon-based oligomers, phosphotriesters can uniquely accommodate side chain attachment directly at their pentavalent connecting phosphate group which allows for a wide diversity of structure and function. To explore these potentially advantageous transporter attributes, we set out to investigate and here report this new class of guanidinium-rich oligophosphoester molecular transporters that have proven to be superior to many other drug/probe delivery systems in various comparative assays.

Guanidinium-rich oligophosphoesters obtained through OROP can accommodate multiple drug delivery strategies depending on the functionality of the cargo drug or probe (FIG. 2). For cargo molecules containing a nucleophilic alcohol, thiol, or amine, a substrate-initiated approach can be used to initiate oligomerization directly with the cargo (FIG. 2, Panel B, Strategy 1). For other, more functionalized drug molecules, a post-oligomerization attachment strategy can be employed (FIG. 2, Panel B, Strategy 2), where a trityl thioether initiator (5) affords a free thiol upon deprotection. Conjugation can occur by reaction of this transporter thiol with a maleimide or iodoacetamide attached to the drug/probe when intracellular drug/probe release is not required (e.g. when a probe or drug's activity is not changed by transporter attachment). If release of free drug is necessary, the transporter thiol can be linked to the drug by a disulfide to afford a redox-releasable drug conjugate. A third strategy (not shown) is to non-covalently complex a polyanionic cargo such as siRNA through electrostatic and hydrogen-bonding interactions as we have shown with guanidinium-rich oligocarbonates. Together, this new class of transporters and these conjugation strategies provide attachment of a wide variety of drug and probe molecules with minimal modification of the method of synthesis and, relative to other comparators, uniquely effective delivery of the resultant conjugates into cells.

Results and Discussion

Design and Synthesis of a Guanidinium-functionalized Cyclic Pholane Monomer for Ring-Opening Oligomerization. A 6-carbon linker was chosen to connect guanidinium groups to the oligophosphoester backbone based on previous optimization of side-chain length on peptoid molecular transporters. The use of this hydrophobic hexyl linker is provided by the increased aqueous solubility of the phosphotriester backbone. The requisite guanidinium-containing monomer was easily prepared by condensative coupling of the corresponding Boc-protected 6-hydroxyhexyl guanidine 2 with 2-chloro-1,3,2-dioxaphospholane-2-oxide (COP) at 0° C. in THF using triethylamine as an HCl scavenger (Scheme 1). Coupling proceeded in nearly quantitative yield, though purification of the resulting monomer, as noted for other cyclic phospholanes, was challenging due to the instability of cyclic phospholanes to heat, moisture, and silica. However, pure monomer 3 was obtained by filtration of triethylammonium salt and removal of solvent and this excess COP under high vacuum, followed by trituration with diethyl ether. The resulting HexPhos monomer was isolated in 79% yield as a highly viscous liquid, which was stored in a glove box in preparation for subsequent oligomerizations.

Scheme 1. Synthesis of protected guanidinylated cyclic phospholane monomer 2-(6-bis-boc guanidino hexyloxy)-1,3,2-dioxaphospholane-2-oxide (HexPhos, 3) from boc-protected 6-guanidino-1-hexanol (2) and 2-chloro-1,3,2-dioxaphospholane-2-oxide.

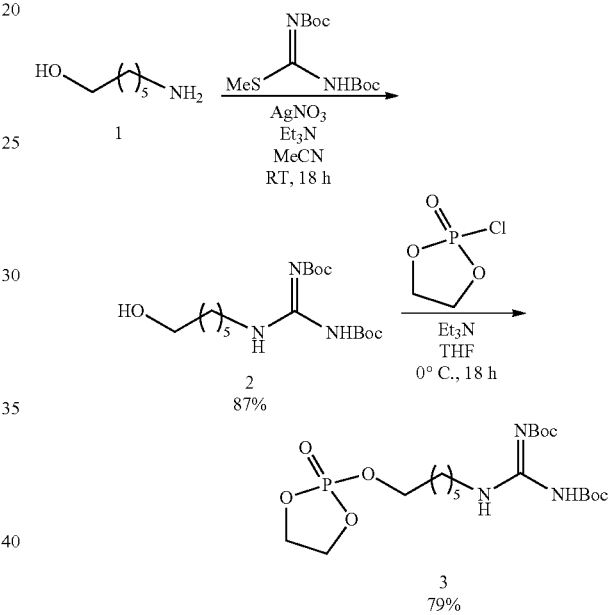

TABLE 1

Guanidinium-functionalized oligomers synthesized by organocatalytic ring-opening oligomerization

| entry | initiator | DP (NMR)[a] | Mn (GPC)[b] | Mw/Mn (GPC)[b] |
|---|---|---|---|---|
| 6a | Dansyl (4) | 8 | 3336 | 1.31 |
| 6b | Dansyl (4) | 10 | 3860 | 1.42 |
| 6c | Dansyl (4) | 12 | 3984 | 1.22 |
| 6d | Dansyl (4) | 18 | 4727 | 1.31 |
| 6e | Dansyl (4) | 25 | 4824 | 1.38 |
| 7 | Trityl-Hexyl (5) | 8 | 3366 | 1.35 |

Figure 6:
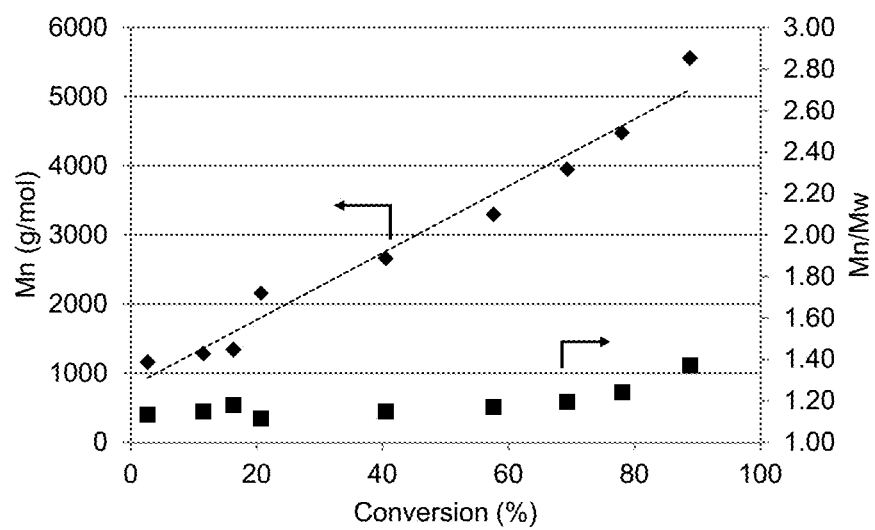
FIG. 6. Molecular weight ($M_n$) vs. conversion of boc-protected HexPhos monomer 3, initiated by Dansyl initiator 4 demonstrating linear chain growth versus conversion and low polydispersity. Relative concentration of initiator to monomer ($[I_o]/[M_0]$)=30. $M_n$ and $M_n/M_w$ determined relative to polystyrene standards by gel permeation chromatography (GPC) in THF.
Figure 7:
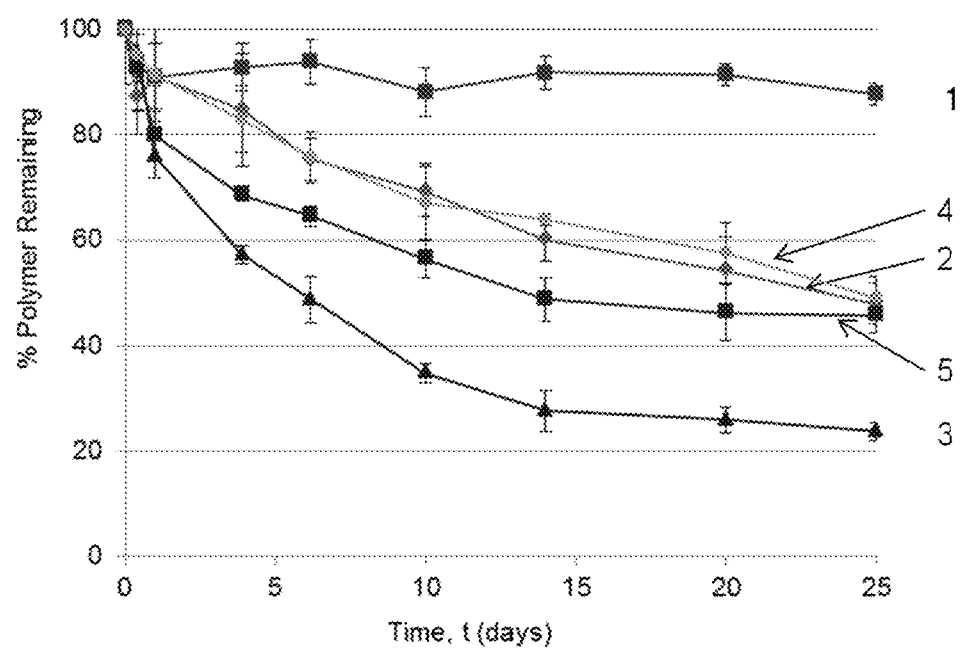
FIG. 7. Relative rates of hydrolysis of HexPhos oligomer 6d as measured by $^{31}$P NMR in acetate buffer, pH 5.0 (1); HEPES buffer, pH 7.4 (2); Tris EDTA, pH 9.0 (3); fetal bovine serum (4), and in the presence of phosphotriesterase I (5). All buffers were made at 0.1 M final concentrations to avoid acidic hydrolysis products affecting pH.

[a]DP calculated by endgroup analysis.
[b]$M_w$ and $M_w/M_n$ determined for protected oligomers by gel permeation chromatography (GPC) in THF relative to polystyrene standards Oligomerization of Hexyl-guanidinium Phospholane Monomer: The synthesis of guanidinium-rich oligophosphoesters was accomplished through OROP of the strained HexPhos monomer 3 following the procedure adapted to phosphotriesters by Yamaguchi and Jérôme (FIG. 2). This strategy has been used by us and others for the synthesis of a variety of linear and cyclic polyphosphoesters. Oligomerizations were conducted under moisture-free conditions in a nitrogen-purged glove box by dissolving HexPhos monomer 3, a primary alcohol initiator (4 or 5), and thiourea catalyst in dichloromethane, followed by addition of 1,8-diazabicycloundec-7-ene (DBU) to catalyze ring-opening. A plot of molecular weight versus conversion is consistent with the living nature of polymerization, showing a linear increase in molecular weight throughout the reaction with conversion up to 88%, and consistent polydispersity ($M_w/M_n$) under 1.4 (FIG. 6).

Using this simple, one-flask procedure, oligomers of a variety of lengths were synthesized by controlling the initiator to monomer ratio (Table 1). By NMR endgroup analysis, degrees of polymerization (DP) were consistent with target monomer/initiator ratios and lengths from 8-25 were obtained, demonstrating the ability of this synthetic method to rapidly produce desired oligomers in a length-selective fashion. Boc-protected oligomers were deprotected by treatment with 10% v/v trifluoroacetic acid in dichloromethane to expose the requisite cationic guanidinium groups. Deprotection occurred in near quantitative yield, resulting in complete loss of Boc group and no reduction in DP or hydrolysis as characterized by $^1$H and $^{31}$P NMR. When the tritylmercaptohexanol initiator (5, strategy 2) was used, 10% v/v ethanedithiol was added after deprotection as a trityl cation scavenger and to reduce any dimers resulting from disulfide formation. All resulting cationic oligomers were freely water and PBS-soluble for use in in vitro assays.

Hydrolytic Stability of HexPhos Oligomers: New guanidinium-rich oligophosphoester transporters exhibited increased hydrolytic and biological stability relative to oligocarbonates. Degree of hydrolysis of HexPhos oligomer 6d (shown in FIG. 2, Panel B, strategy 1) was monitored for 25 days by $^{31}$P NMR by comparing the relative areas of phosphotriester $^{31}$P peaks ($\delta$=−2 to −3), indicative of intact oligomeric units, and phosphodiester or monoester $^{31}$P peaks ($\delta$=2 to −2), indicating a hydrolysis product. In acetate buffer (pH 5.0, consistant with late endosomes/lysosomes and skin), the oligomer showed a high degree of hydrolytic stability, with only approximately 10% degradation occurring after 25 days. Neutral conditions (HEPES buffer pH 7.4, cytosol and bloodstream) afforded modest degradation, with a half-life of approximately 22 days. The fastest rates of hydrolysis occurred under basic conditions (Tris-HCl buffer pH 9.0, mitochondria and intestinal tract), with an approximate half-life of 6 days. The same pH-dependence of hydrolysis has been observed for amine-functionalized phosphotriesters, while oligomers with aliphatic or neutral side chains show no increase in hydrolysis under basic conditions. HexPhos oligomers appeared to be inert to cleavage by Phosphotriesterase I an enzyme that previous reports have shown to catalyze the hydrolysis of simple linear phosphoesters, with hydrolysis rates being similar to those in neutral (pH7.4) buffer. This is advantageous for their utility in the bloodstream, GI tract, and tumor tissues where phosphatase concentrations are known to be elevated. Incubation in fetal bovine serum (FBS) afforded hydrolysis rates very similar to the neutral buffered condition, indicating that the presence of other biomolecules and serum proteins does not significantly affect backbone degradation. These hydrolysis properties demonstrate that the oligophosphoester backbone is significantly more robust than previously studied polycarbonate ($t_{1/2}$=8 h) and polyester ($t_{1/2}$=1-3 h) systems. The increased hydrolytic stability allows for ease of storage, formulation and treatment, while still maintaining biodegradability to non-toxic components over longer time periods.

Substrate-initiated delivery of a fluorescent probe by HexPhos oligomers: The new guanidinium-rich oligophosphoesters demonstrated increased efficacy as drug delivery vehicles relative to previously studied oligopeptides and oligocarbonates. To evaluate the cellular uptake of HexPhos molecular transporters, HeLa cells were treated with oligomers and analyzed by flow cytometry for the fluorescence of the dansyl sulfonamide probe 4 used as an initiator. The dansyl probe 4 alone has been previously shown not to enter cells without attachment to a transporter. Using this assay, the relative efficiency of a variety of oligomers can be quantified and compared, and applied to future cargo-conjugates obtained through Strategy 1 or Strategy 2 in FIG. 2, panel B. First, an oligomer length screen was performed to determine the dependence of cellular uptake on the number of guanidinium groups in an oligomer (FIG. 3), and to compare the HexPhos oligomers to the arginine homo-oligomer (Dansyl-Arg8, 8) and the oligocarbonate system reported by Cooley, et al (Dansyl-MTC-G8, 9). This screen showed maximal uptake occurring with the HexPhos 10-mer 6b. This is consistent with our previous work on peptoid molecular transporters which showed a parabolic relationship of length and uptake with 16-mers being optimal. The decrease in uptake for the HexPhos 18-mer (6d) and 25-mer (6e) is likely due to increased toxicity, with cells treated with those compounds appearing less viable than cells treated with shorter oligomers.

Figure 3A:
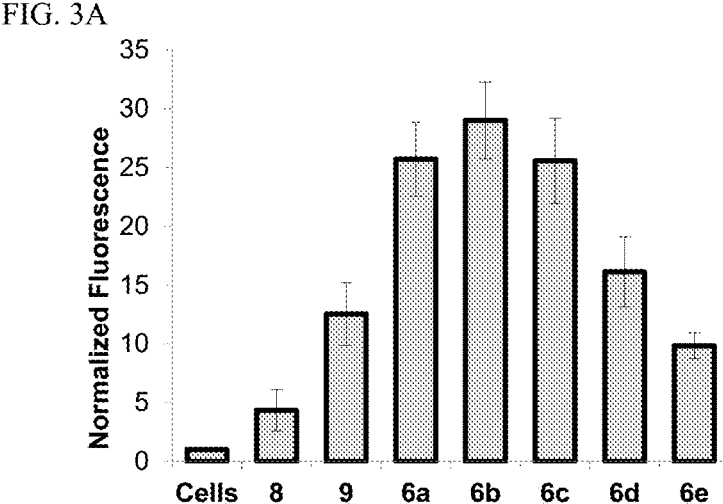
FIG. 3A-3C. Uptake of Dansyl-HexPhos oligomers compared to previously studied transporters.
Figure 3B:
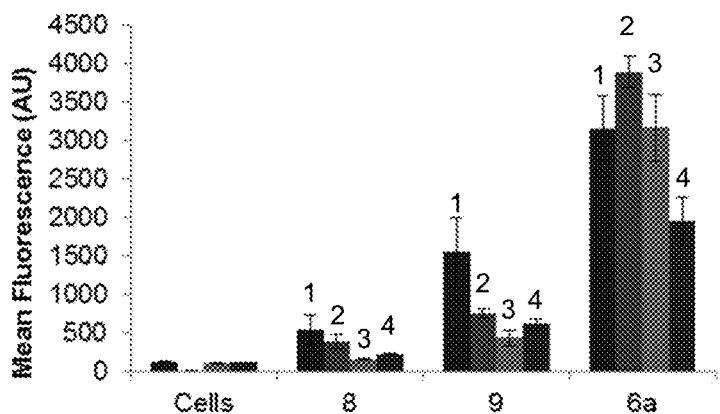
Figure 3C:
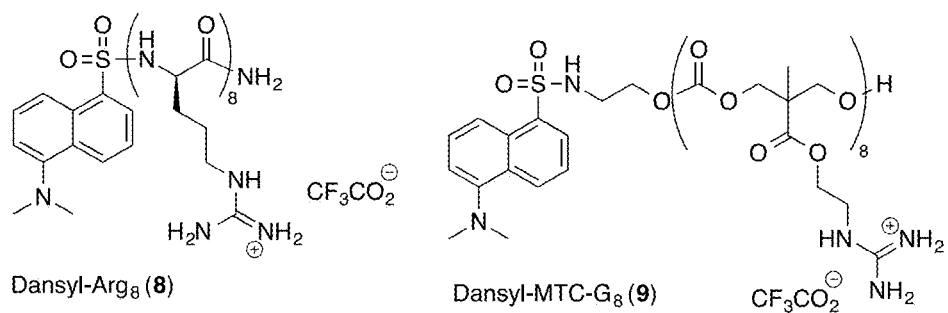

As illustrated in FIG. 3, the superior performance of the Dansyl-HexPhos8 relative to the Dansyl-Arg8 (8) and Dansyl-MTC-G8 (9) transporters is dramatic. HexPhos oligomers were taken into cells to higher degrees than both previously reported systems, with >6-fold increases in fluorescence over the peptide Dansyl-Arg8 (8) and a >2-fold increase over the oligocarbonate Dansyl-MTC-G8 (9). This increase in uptake can be explained by the increased linker length (6-carbons) over the oligocarbonate system (2-carbons), allowing the guanidinium groups to more effectively access and hydrogen bond cell surface distributed anions (e.g., phosphates, sulfates, and carboxylates) as proposed for initiation of cell entry. The increased hydrophobic density of this linker also allows for easier partitioning into the membrane after initial association occurs. Longer side chains on other transporter systems encountered a loss in solubility not observed with these oligophosphorester transporters.

Figure 8:
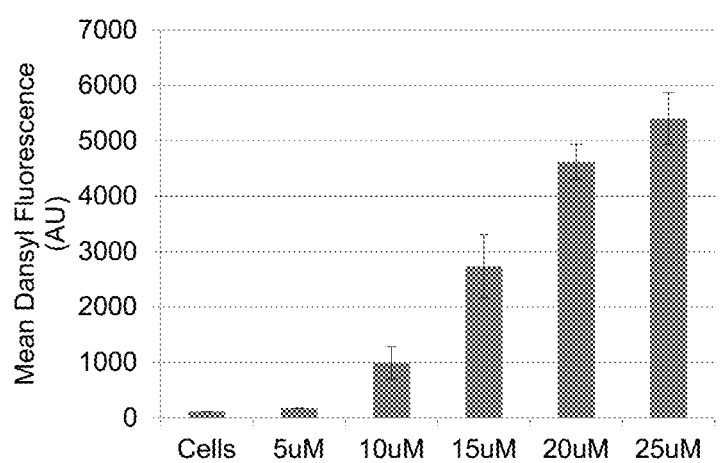
FIG. 8. Concentration dependence of uptake of Dansyl-HexPhos8 oligomer 6a in HeLa cells. Cells were treated with compound for 10 minutes at 35° C. and the mean fluorescence determined by flow cytometry. Values represent the average of at least 10,000 cells measured in each experiment. The data shown are the average of at least 3 separate experiments with error bars representing the standard deviation.
Figure 9:
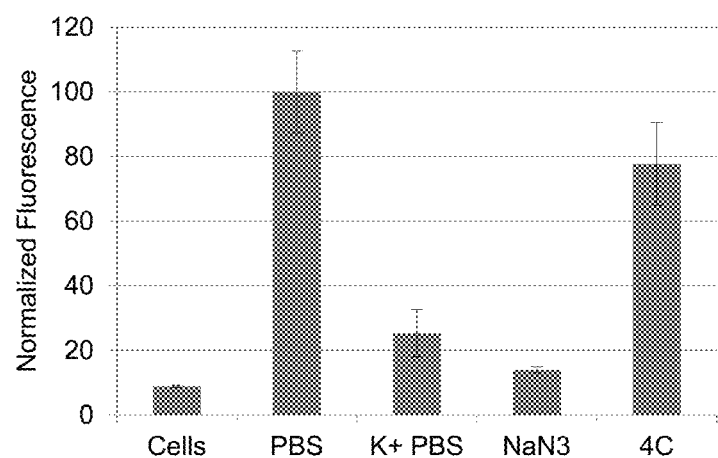
FIG. 9. Mechanistic study of uptake of Dansyl-HexPhos8 oligomer 6a in HeLa cells. Prior to treatment, cells were treated with conditions designed to attenuate a given uptake mechanism. Following pre-treatment with high-potassium PBS, sodium azide, or at 4° C., cells were treated with Dansyl-HexPhos8 (6a) in the same condition, and the uptake measured by flow cytometry. Values represent the average of at least 10,000 cells measured in each experiment, and were normalized to standard uptake in PBS. The data shown are the average of at least 3 separate experiments with error bars representing the standard deviation.

Dose and cell line dependence of uptake of HexPhos oligomers. The generality of cellular uptake was explored by testing oligomer internalization in a variety of human and non-human cancer cell lines (FIG. 3, panel B). The Dansyl-HexPhos8 oligomer 6a was selected for analysis on the basis that it showed robust uptake and would be directly comparable to previously studied Dansyl-Arg8 (8) and Dansyl-MTC-G8 (9) systems. HeLa cells (human cervical cancer) were used along with Jurkat (human T-lymphocytes), OVCAR-429 (human ovarian cancer), and 4T1 (murine breast cancer) cells. Significantly, all cell lines showed robust uptake, with the HexPhos 8-mer 6a out-performing both the Dansyl-Arg8 (8) and Dansyl-MTC-G8 (9) controls. This widens the breadth of potential applications for the HexPhos delivery system. Dansyl-HexPhos8 6a shows a linear dependence on treatment concentration in HeLa cells from 5 uM to 25 uM concentrations (FIG. 8). The lower bound of this range is limited only by the detection limits of the dansyl fluorophore by flow cytometry, with much lower treatment concentrations possible.

Cellular toxicity: HexPhos oligomers exhibit low levels of cellular toxicity in MTT viability assays. Compound toxicity increased slightly with oligomer length, a trend that was also demonstrated in other systems such as the peptides and oligocarbonates. However, toxicity thresholds for all compounds were well above typical treatment concentrations for typical molecular therapeutics or imaging probes. $LD_{50}$'s were measured at 18 µM, 12 µM, 10 µM, 9 µM, and 3 µM for the 8-mer (6a), 10-mer (6b), 12-mer (6c), 16-mer (6d) and 25-mer (6e) respectively (Table 3).

TABLE 3

Compiled MTT-determined LD50 (the amount of compound required to reduce cellular viability by half) values for HexPhos oligomers in HeLa cells. Cells were treated with compounds for 10 minutes at 35° C. and their viability assessed relative to untreated controls.

| Compound | $LD_{50}$ (µM) HeLa cells |
|---|---|
| Dansyl-MTC-G8 (9) | 36.04 ± 5.55 |
| Dansyl-HexPhos8 (6a) | 18.03 ± 1.72 |
| Dansyl-HexPhos10 (6b) | 11.58 ± 1.60 |
| Dansyl-HexPhos12 (6c) | 9.54 ± 1.23 |
| Dansyl-HexPhos18 (6d) | 6.40 ± 2.28 |
| Dansyl-HexPhos25 (6e) | 3.44 ± 0.48 |

Mechanism of uptake: To gather insight into the mechanism of uptake of Dansyl-HexPhos8 (6a) and compare these results to other transporter systems, several conditions previously shown to influence uptake were examined. When cells were incubated with Dansyl-HexPhos8 in PBS where sodium ions were replaced with potassium ions, a condition known to reduce the membrane potential, uptake was reduced by 75%. In line with our earlier studies, this result indicates that the membrane potential is required in the mechanism for uptake of the new transporters. When cells were treated with Dansyl-HexPhos8 (6a) at 4° C., a condition which attenuates endocytotic activity, there was a 25% reduction in uptake. Taken together, these results suggest mixed mechanisms of cellular entry with a non-endocytic mechanism playing a dominant role. Such dual or competing mechanisms have been observed previously in single molecule experiments. Sodium azide inhibits ATP-dependent processes which inhibits both endocytosis and neutralizes the membrane potential by disabling sodium-potassium exchange pumps. Treatment with $NaN_3$ resulted in significant (86%) reduction in uptake consistent with inhibition of multiple uptake mechanisms. Additional mechanistic studies will be reported separately as uptake is known to be influenced by cargo size, temperature, cell type, counterion and other factors.

Figure 4A:
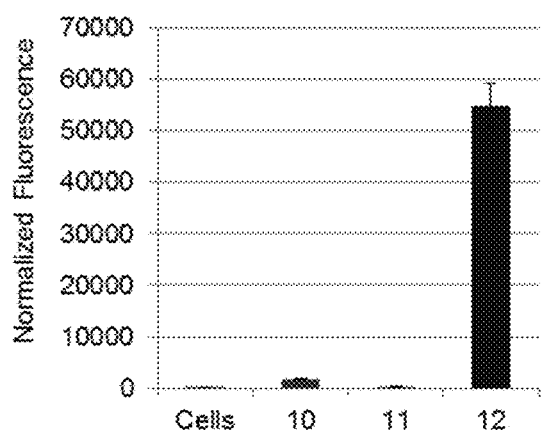
FIG. 4A-4C.
Figure 4B:
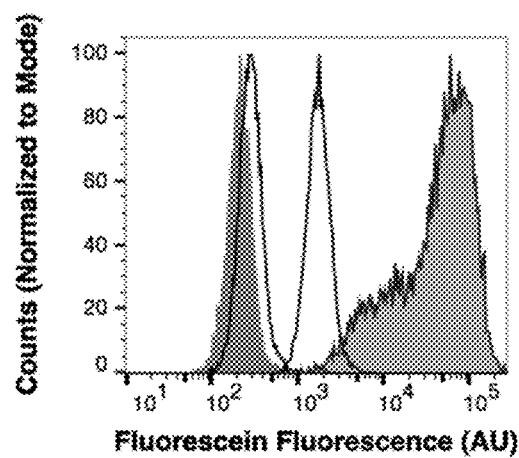
Figure 4C:
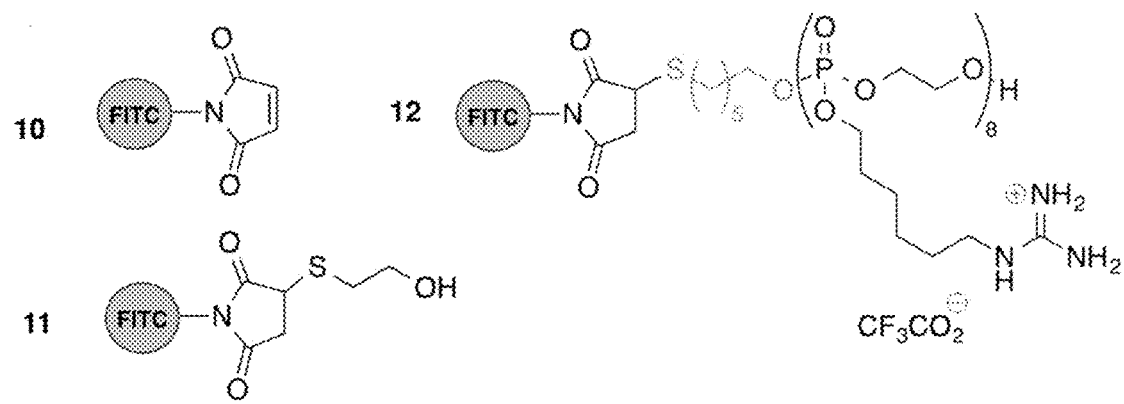

Delivery of thiol-reactive probes: A wide scope of drug and probe molecules can be installed post-oligomerization using a protected thiol initiator (5) as shown in FIG. 2, panel B, Strategy 2. This "clickable" conjugation strategy allows for attachment and delivery of drugs containing reactive functionalities that are not compatible with the organocatalytic polymerization or deprotection conditions. Many fluorescent probes, small-molecule therapeutics, and peptides are available as maleimide or iodoacetamide conjugates, and can thus be attached in situ to a thiol-functionalized oligomer immediately before treatment. To explore this strategy, deprotected thiol-initiated HexPhos 8-mer (7) was mixed with fluorescein (FL) maleimide (10) in PBS at room temperature for 2 hours to effect a Michael addition and uptake of the resulting conjugate was determined by flow cytometry (FIG. 4, panel A). Cells treated with the FL-maleimide control 10 showed little FL fluorescence, likely only arising from reaction of nucleophiles present on the cell surface. In line with this reasoning, when the FL-maleimide conjugate was pre-reacted with mercaptoethanol to form control conjugate 11, fluorescence was further reduced. In striking contrast, the FL-HexPhos conjugate 12 showed a 160-fold increase in fluorescence over the control compounds 10 and 11 in line with significant cellular uptake. Treated cells showed a complete shift in population (>99% transfection) as shown in the flow cytometry histogram (FIG. 4, panel B). This demonstrates the viability of maleimide coupling or other thiol-click reactions for delivery of probes or drugs where release is not a requirement for activity.

Figure 5:
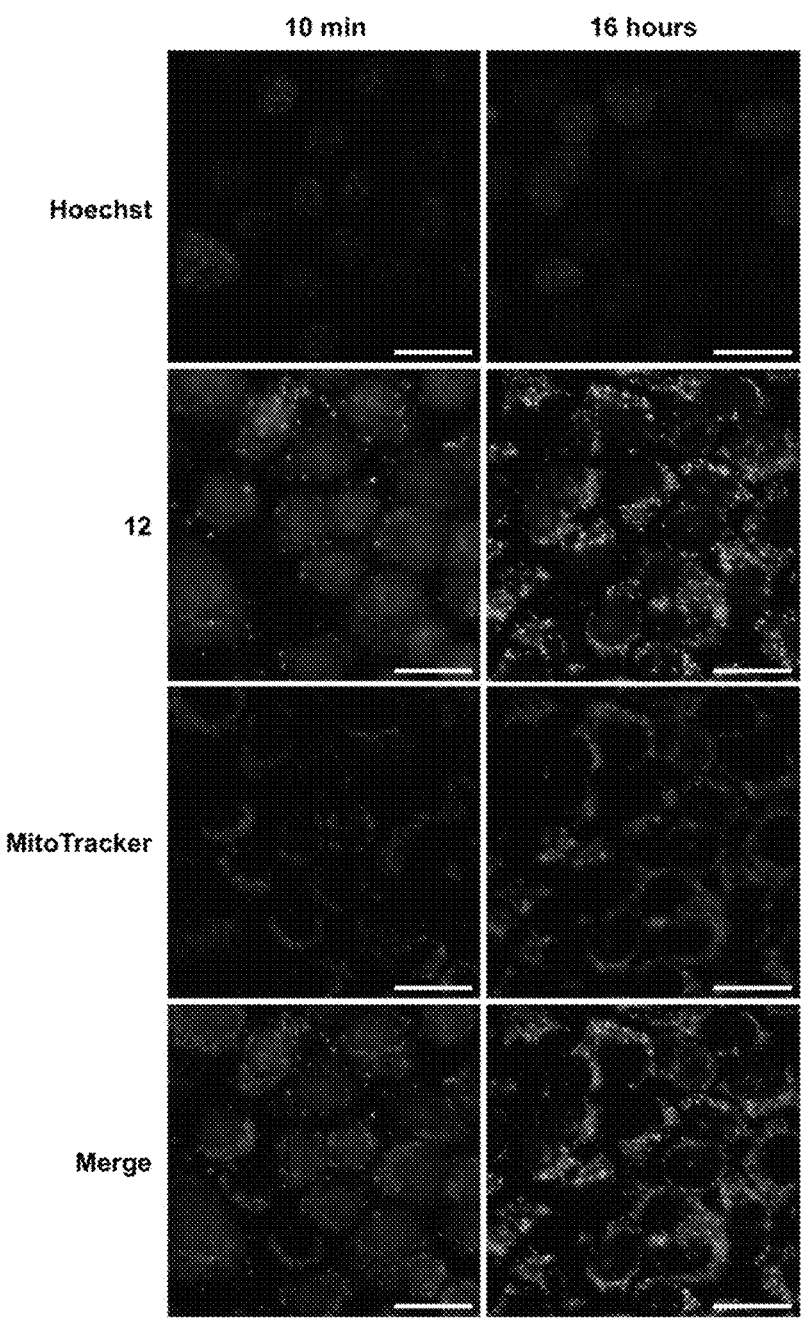
FIG. 5. Confocal microscopy images of HeLa cells treated with FL-HexPhos8 conjugate 12 (10 µM) for 10 minutes. Cell nuclei were counterstained with Hoechst 33342 and mitochondria stained with MitoTracker prior to imaging. Images were taken 10 minutes and 16 hours following treatment.

Intracellular Localization of HexPhos oligomers. Confocal microscopy was used to further assess the intracellular localization of HexPhos oligomers, and to confirm that flow cytometry results were reflective of HexPhos localization inside cells as opposed to attached to the cellular surface. FL-HexPhos8 conjugate 12 was chosen due to the brighter fluorescein fluorophore. Imaging was done at two time points to observe intracellular localization immediately following (t=10 minutes), and 16 hours after treatment (FIG. 5). Z-slices through the cellular equator at both timepoints show a large degree of staining within the cell body, with little fluorophore adhesion to the membrane. Ten minutes following treatment, fluorescence was highly diffuse with a few bright puncta, which is consistent with above mechanistic results showing a predominantly endocytosis-independent mechanism of entry. After 16 hours of incubation, fluorescent staining becomes much more punctate and localizes around the nucleus, which is hypothesized to be the result of mitochondrial accumulation. Co-incubation of HeLa cells with FL-HexPhos8 conjugate 12 and MitoTracker, a commercial agent designed to accumulate in mitochondria, confirmed co-localization of stained regions.

Figure 10:
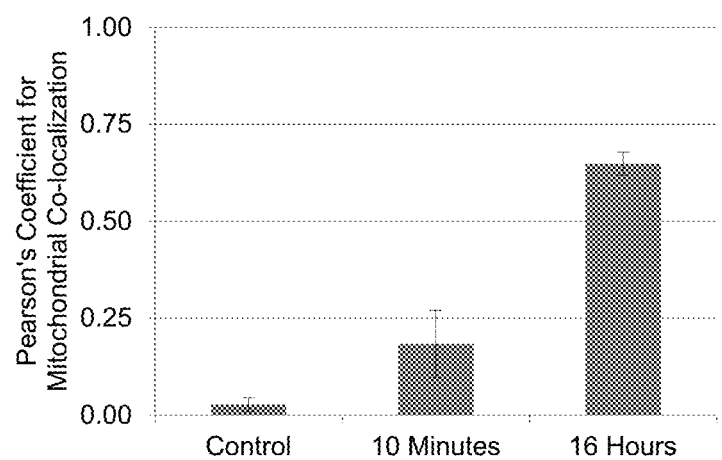
FIG. 10. Pearson's Correlation Coefficient (PCC) results for cells co-treated with FL-HexPhos8 conjugate 12 and MitoTracker mitochondrial stain. Co-localization was measured immediately following treatment (10 minutes) and after 16 hours of incubation. Control was determined by measuring the PCC for images rotated 90° from each other as a negative control. The data shown are the average of 3 images each showing at least 10 cells, with the error bars representing the standard deviation.
Figure 11:
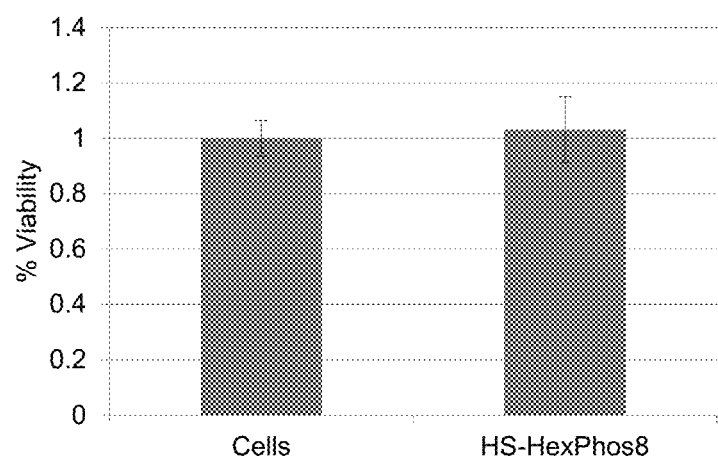
FIG. 11. Viability of unconjugated HexPhos oligomer (7) relative to untreated controls. Cells were treated at 5 µM oligomer concentration for 20 minutes and viability assessed by MTT toxicity assay. The data shown are the average of at least 3 separate experiments with error bars representing the standard deviation.

Pearson's Correlation Coefficient (PCC provides a quantitative measure of the increase in co-localization levels from a low PCC of 0.18±0.09 after 10 minutes to a relatively high PCC of 0.65±0.03 after 16 hours (FIG. 10), supports the conclusion that oligomers enter the cell non-endocytotically, and later accumulate in the mitochondria. Amphipathic guanidinium-rich oligopeptides accumulate in the mitochondria due to increased hydrophobic interactions with the inner mitochondrial membrane, and delocalization of charge by a mixed amphipathic scaffold, which aligns with the structure of the HexPhos oligomers. This localization could be exploited by delivering chemotherapeutic agents such as chlorambucil directly to the mitochondria for increased efficacy, but does not preclude cytosolic delivery and release of free drug/probe (such as through a reducible disulfide) as transporters would still spend ample time in the cytosol for release to occur.

Synthesis and evaluation of PTX-HexPhos Conjugates: In order to explore the utility of the HexPhos backbone in a more challenging and therapeutically important delivery scenario, paclitaxel (PTX)-HexPhos conjugates were synthesized and their activity against PTX-resistant ovarian cancer cells evaluated. Our prior work with cultured and primary drug-resistant cancer cells demonstrated that $Arg_8$-drug conjugates overcome drug resistance putatively by avoiding Pgp-related efflux, but these results have not been addressed with an oligomeric scaffold. Because resistance is often the major cause of chemotherapy failure, we set out to test this strategy for overcoming resistance with our new transporter scaffold.

Releasable PTX conjugates were synthesized by disulfide exchange between a thiol-initiated oligomer and an activated pyridyl disulfide drug conjugate (FIG. 2, Strategy 2). The resulting disulfide-linked drug-transporter conjugate is shelf stable and enters cells by a mechanism that evades Pgp export. Once in the cytosol the conjugate encounters high glutathione concentrations (15 mM intracellular vs. 15 μM extracellular) causing cleavage of disulfide bond,[22] and subsequent drug release in the cytosol. PTX-HexPhos conjugate 16 was synthesized as shown in Scheme 2 by disulfide exchange between a thiol-initiated oligomer 7 and C2′-pyridyl disulfide paclitaxel (15). Following removal of excess PTX by precipitation, oligomers showed 50% drug incorporation by NMR endgroup analysis. Molecular weights by MALDI show an increase in molecular weight consistent with attachment of PTX and linker to make the final conjugate 16. Subsequently reported concentrations are based on paclitaxel content.

MALDI analysis of PTX-HexPhos8 conjugate. Sample was ionized out of DHB matrix in linear/positive ion mode. Monomer spacing of 265 Da is consistent with the HexPhos monomer, and endgroup MW of 1088 Da is consistant with paclitaxel and disulfide linker.

Scheme 2.
Synthesis of PTX-HexPhos conjugate 16 by disulfide exchange of activated PTX-disulfide 15 and thiol-initiated HexPhos oligomer 7.

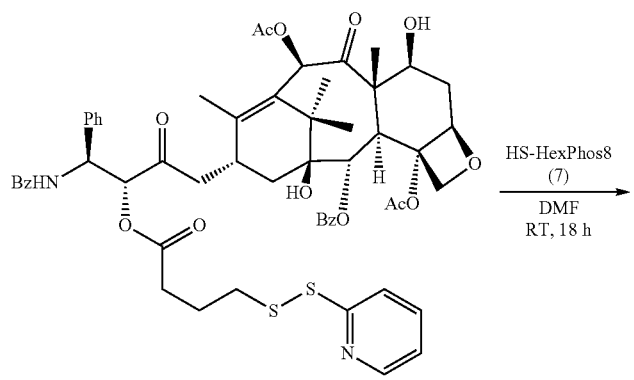

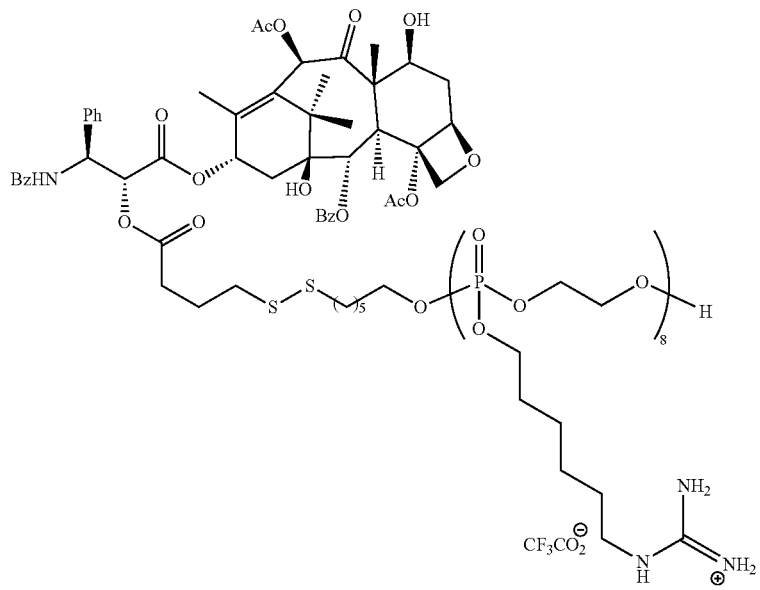

The in vitro efficacy of PTX-HexPhos conjugate 16 was compared to free PTX in both wild-type and PTX-resistant ovarian cancer cells engineered to have high levels of Pgp up-regulation. OVCA-429 (wild-type) and OVCA-429T (resistant) cells were treated with free PTX (14) or the HexPhos conjugate 16 for 20 minutes in PBS, then washed and incubated for 3 days. After this time, cellular viability was assessed using a standard MTT assay to generate an $EC_{50}$ value (the concentration at which overall cellular viability was half that of untreated cells) for each condition. As expected, in wild-type OVCA-429 cells both free PTX (14) and the PTX-HexPhos conjugate 16 were highly cytotoxic (Table 2). However, in the drug-resistant OVCA-429T cells, PTX alone was unable to kill cells at any concentration up to the limit of the assay (20 µM). In striking contrast, the HexPhos conjugate 16 was still able to maintain efficacy with only a modest increase in $EC_{50}$ to 1.36 µM. To verify that the oligomer itself was not contributing to the cytotoxicity of the conjugate, OVCA-429T cells were also treated with the un-conjugated HexPhos oligomer 7. As expected the $EC_{50}$ for the oligomer alone was nearly an order of magnitude higher than this, with >95% viability up to 5 µM. The efficacy of these compounds can be expressed in terms of a "resistance factor" for free PTX and the HexPhos-paclitaxel conjugate 16, defined as the $EC_{50}$ in resistant cells/the $EC_{50}$ in wild-type cells. PTX alone (14) succumbs readily to resistance, with a resistance factor of 400 or greater. The PTX-HexPhos conjugate 16, however, shows a resistance factor of only 5.2, demonstrating the relatively small (5-fold) increase in $EC_{50}$ for resistant disease.

TABLE 2

Cellular toxicity ($EC_{50}$) for free PTX and PTX-HexPhos conjugates in wild-type, and resistant OVCA-429 ovarian cancer cells.

| Compound | $EC_{50}$ (µM)[a] | | |
|---|---|---|---|
| | OVCA-429 (Wild-type) | OVCA-429T (Resistant) | Resistance Factor[b] |
| PTX Alone (14) | 0.051 ± 0.037 | >20 | >400 |
| PTX-HexPhos8 (16) | 0.26 ± 0.073 | 1.4 ± 0.45 | 5.2 |
| HS-HexPhos8 (7) | — | 13 ± 2.9 | — |

[a]Determined by treating cells for 20 minutes with compounds, followed by a wash and incubation in drug-free media for 72 hours and determining viability by MTT assay. All values are the result of three separate experiments, each performed in triplicate with error being the standard deviation.
[b]Resistance Factor = $EC_{50}$ (Wild-type)/$EC_{50}$ (Resistant)

We have described the design, synthesis, and biological evaluation of a new class of guanidinium-rich oligophosphoester delivery vehicles. These oligomeric transporters are easily prepared in any length from cyclic monomers in a single oligomerization step and subsequent deprotection in high yield with low polydispersity. Drugs or probes are readily attached in one step as oligomerization initiators. Oligomers produced using this method and initiated by a fluorescent probe exhibit high levels of uptake in multiple cell lines. This cellular uptake varies as a function of oligomer length and maximizes at an average of 10 monomer units. Significantly, cellular uptake is substantially higher than the best previously reported oligoarginine and oligocarbonate systems, among the best performers reported thus far. In addition to their conjugation with drug or probe initiators, these oligomers can also be conjugated to probes (e.g., fluorescein-maleimide) and drugs (e.g., paclitaxel) through a thiol intitiator using a simple, "kit-style" preparation. The resulting non-releasable fluorescein conjugates show high levels of cell entry as demonstrated by flow cytometry and confocal microscopy. A releasable paclitaxel-transporter conjugate designed to release free paclitaxel intracellularly was shown to overcome PTX-resistant ovarian cancer cells. The ability to convert a drug that is ineffective against resistant disease to one that is effective by simple conjugation to a transporter provides the basis for addressing a major unmet clinical need associated with multidrug resistance. This concept should be applicable to other drugs that are Pgp substrates and that succumb to Pgp export based resistance. These oligophosphoesters represent an especially versatile new class of easily-prepared and hydrolytically stable drug delivery vehicles that are proving to be superior to other oligomeric transporters in all comparative studies thus far and can be readily conjugated with drugs and probes as needed for a variety of clinical, preclinical, and basic research applications.

REFERENCES

Wender, P. A.; Cooley, C. B.; Geihe, E. I. *Drug Discov. Today Technol.* 2011.
Stanzl, E. G.; Trantow, B. M.; Vargas, J. R.; Wender, P. A. *Acc. Chem. Res.* 2013, 46 (12), 2944.
Wender, P. A.; Mitchell, D. J.; Pattabiraman, K.; Pelkey, E. T.; Steinman, L.; Rothbard, J. B. *Proc. Natl. Acad. Sci.* 2000, 97 (24), 13003.
Rothbard, J. B.; Jessop, T. C.; Lewis, R. S.; Murray, B. A.; Wender, P. A. *J. Am. Chem. Soc.* 2004, 126 (31), 9506.
Mitchell, D. j.; Steinman, L.; Kim, D. t.; Fathman, C. g.; Rothbard, J. b. *J. Pept. Res.* 2000, 56 (5), 318.
Rothbard, J. B.; Kreider, E.; VanDeusen, C. L.; Wright, L.; Wylie, B. L.; Wender, P. A. *J. Med. Chem.* 2002, 45 (17), 3612.
Wender, P. A.; Rothbard, J. B.; Jessop, T. C.; Kreider, E. L.; Wylie, B. L. *J. Am. Chem. Soc.* 2002, 124 (45), 13382.
Wender, P. A.; Kreider, E.; Pelkey, E. T.; Rothbard, J.; VanDeusen, C. L. *Org. Lett.* 2005, 7(22), 4815.
Cooley, C. B.; Trantow, B. M.; Nederberg, F.; Kiesewetter, M. K.; Hedrick, J. L.; Waymouth, R. M.; Wender, P. A. *J. Am. Chem. Soc.* 2009, 131 (45), 16401.
Rueping, M.; Mahajan, Y.; Sauer, M.; Seebach, D. *ChemBioChem* 2002, 3 (2-3), 257.
Futaki, S.; Nakase, I.; Suzuki, T.; Zhang; Sugiura, Y. *Biochemistry (Mosc.)* 2002, 41 (25), 7925.
Fillon, Y. A.; Anderson, J. P.; Chmielewski, J. *J. Am. Chem. Soc.* 2005, 127(33), 11798.
Lättig-Tünnemann, G.; Prinz, M.; Hoffmann, D.; Behlke, J.; Palm-Apergi, C.; Morano, I.; Herce, H. D.; Cardoso, M. C. *Nat. Commun.* 2011, 2, 453.
Qian, Z.; Liu, T.; Liu, Y.-Y.; Briesewitz, R.; Barrios, A. M.; Jhiang, S. M.; Pei, D. *ACS Chem. Biol.* 2013, 8 (2), 423.
Zhou, P.; Wang, M.; Du, L.; Fisher, G. W.; Waggoner, A.; Ly, D. H. *J. Am. Chem. Soc.* 2003, 125 (23), 6878.
Kolonko, E. M.; Kiessling, L. L. *J. Am. Chem. Soc.* 2008, 130 (17), 5626.
Tezgel, A. Ö.; Telfer, J. C.; Tew, G. N. *Biomacromolecules* 2011, 12 (8), 3078.
Treat, N. J.; Smith, D.; Teng, C.; Flores, J. D.; Abel, B. A.; York, A. W.; Huang, F.; McCormick, C. L. *ACS Macro Lett.* 2012, 1 (1), 100.
Gasparini, G.; Bang, E.-K.; Molinard, G.; Tulumello, D. V.; Ward, S.; Kelley, S. O.; Roux, A.; Sakai, N.; Matile, S. *J. Am. Chem. Soc.* 2014, 136 (16), 6069.
Rothbard, J. B.; Garlington, S.; Lin, Q.; Kirschberg, T.; Kreider, E.; McGrane, P. L.; Wender, P. A.; Khavari, P. A. *Nat. Med.* 2000, 6 (11), 1253.

Luedtke, N. W.; Carmichael, P.; Tor, Y. *J. Am. Chem. Soc.* 2003, 125 (41), 12374.

Jones, L. R.; Goun, E. A.; Shinde, R.; Rothbard, J. B.; Contag, C. H.; Wender, P. A. *J. Am. Chem. Soc.* 2006, 128 (20), 6526.

Chen, L.; Wright, L. R.; Chen, C.-H.; Oliver, S. F.; Wender, P. A.; Mochly-Rosen, D. *Chem. Biol.* 2001, 8(12), 1123.

Jameson, K. L.; Mazur, P. K.; Zehnder, A. M.; Zhang, J.; Zarnegar, B.; Sage, J.; Khavari, P. A. *Nat. Med.* 2013, 19 (5), 626.

Schwarze, S. R.; Ho, A.; Vocero-Akbani, A.; Dowdy, S. F. *Science* 1999, 285 (5433), 1569.

Zhou, H.; Wu, S.; Joo, J. Y.; Zhu, S.; Han, D. W.; Lin, T.; Trauger, S.; Bien, G.; Yao, S.; Zhu, Y.; Siuzdak, G.; Schöler, H. R.; Duan, L.; Ding, S. *Cell Stem Cell* 2009, 4 (5), 381.

Kumar, P.; Wu, H.; McBride, J. L.; Jung, K.-E.; Hee Kim, M.; Davidson, B. L.; Kyung Lee, S.; Shankar, P.; Manjunath, N. *Nature* 2007, 448 (7149), 39.

Geihe, E. I.; Cooley, C. B.; Simon, J. R.; Kiesewetter, M. K.; Edward, J. A.; Hickerson, R. P.; Kaspar, R. L.; Hedrick, J. L.; Waymouth, R. M.; Wender, P. A. *Proc. Natl. Acad. Sci.* 2012, 109 (33), 13171.

Wender, P. A.; Huttner, M. A.; Staveness, D.; Vargas, J. R.; Xu, A. F. *Mol. Pharm.* 2015, 12 (3), 742.

Siprashvili, Z.; Scholl, F. A.; Oliver, S. F.; Adams, A.; Contag, C. H.; Wender, P. A.; Khavari, P. A. *Hum. Gene Ther.* 2003, 14 (13), 1225.

Torchilin, V. P.; Levchenko, T. S.; Rammohan, R.; Volodina, N.; Papahadjopoulos-Sternberg, B.; D'Souza, G. G. M. *Proc. Natl. Acad. Sci.* 2003, 100 (4), 1972.

Wender, P. A.; Galliher, W. C.; Goun, E. A.; Jones, L. R.; Pillow, T. H. *Adv. Drug Deliv. Rev.* 2008, 60 (4), 452.

Torchilin, V. P. *Adv. Drug Deliv. Rev.* 2008, 60 (4-5), 548.

Hyman, J. M.; Geihe, E. I.; Trantow, B. M.; Parvin, B.; Wender, P. A. *Proc. Natl. Acad. Sci. U.S.A.* 2012, 109 (33), 13225.

Zhao, Z.; Wang, J.; Mao, H.-Q.; Leong, K. W. *Adv. Drug Deliv. Rev.* 2003, 55 (4), 483.

Monge, S.; Canniccioni, B.; Graillot, A.; Robin, J.-J. *Biomacromolecules* 2011, 12 (6), 1973.

Steinbach, T.; Wurm, F. R. *Angew. Chem. Int. Ed.* 2015, 54 (21), 6098.

Penczek, S.; Pretula, J. *Macromolecules* 1993, 26 (9), 2228.

Lapienis, G.; Penczek, S. *Macromolecules* 1974, 7(2), 166.

Lapienis, G.; Penczek, S.; Pretula, J. *Macromolecules* 1983, 16 (2), 153.

Klosinski, P.; Penczek, S. *Macromolecules* 1983, 16 (2), 316.

Zhang, S.; Zou, J.; Zhang, F.; Elsabahy, M.; Felder, S. E.; Zhu, J.; Pochan, D. J.; Wooley, K. L. *J. Am. Chem. Soc.* 2012, 134 (44), 18467.

Zhang, F.; Zhang, S.; Pollack, S. F.; Li, R.; Gonzalez, A. M.; Fan, J.; Zou, J.; Leininger, S. E.; Pavía-Sanders, A.; Johnson, R.; Nelson, L. D.; Raymond, J. E.; Elsabahy, M.; Hughes, D. M. P.; Lenox, M. W.; Gustafson, T. P.; Wooley, K. L. *J. Am. Chem. Soc.* 2015, 150128123919002.

Zou, J.; Zhang, F.; Zhang, S.; Pollack, S. F.; Elsabahy, M.; Fan, J.; Wooley, K. L. *Adv. Healthc. Mater.* 2014, 3 (3), 441.

Wang, J.; Mao, H.-Q.; Leong, K. W. *J. Am. Chem. Soc.* 2001, 123 (38), 9480.

Kiesewetter, M. K.; Shin, E. J.; Hedrick, J. L.; Waymouth, R. M. *Macromolecules* 2010, 43 (5), 2093.

Baran, J.; Penczek, S. *Macromolecules* 1995, 28 (15), 5167.

Wender, P. A.; Goun, E. A.; Jones, L. R.; Pillow, T. H.; Rothbard, J. B.; Shinde, R.; Contag, C. H. *Proc. Natl. Acad. Sci.* 2007, 104 (25), 10340.

Lim, Y. H.; Heo, G. S.; Rezenom, Y. H.; Pollack, S.; Raymond, J. E.; Elsabahy, M.; Wooley, K. L. *Macromolecules* 2014, 47(14), 4634.

Iwasaki, Y.; Yamaguchi, E. *Macromolecules* 2010, 43 (6), 2664.

Clément, B.; Grignard, B.; Koole, L.; Jérôme, C.; Lecomte, P. *Macromolecules* 2012, 45 (11), 4476.

Stukenbroeker, T. S.; Solis-lbarra, D.; Waymouth, R. M. *Macromolecules* 2014, 47 (23), 8224.

Steinbach, T.; Schroder, R.; Ritz, S.; Wurm, F. R. *Polym. Chem.* 2013, 4 (16), 4469.

Wang, Y.-C.; Tang, L.-Y.; Sun, T.-M.; Li, C.-H.; Xiong, M.-H.; Wang, J. *Biomacromolecules* 2008, 9 (1), 388.

Baran, J.; Kaluzynski, K.; Szymanski, R.; Penczek, S. *Biomacromolecules* 2004, 5 (5), 1841.

Stella, V. J.; Nti-Addae, K. W. *Adv. Drug Deliv. Rev.* 2007, 59 (7), 677.

Warnes, T. W. *Gut* 1972, 13 (11), 926.

Domar, U.; Hirano, K.; Stigbrand, T. *Clin. Chim. Acta* 1991, 203 (2-3), 305.

Zhang, Z.; Ortiz, O.; Goyal, R.; Kohn, J. *In Principles of Tissue Engineering (Fourth Edition)*; Lanza, R., Langer, R., Vacanti, J., Eds.; Academic Press: Boston, 2014; pp 441-473.

Gombotz, W. R.; Pettit, D. K. *Bioconjug. Chem.* 1995, 6 (4), 332.

Lynn, D. M.; Langer, R. *J. Am. Chem. Soc.* 2000, 122 (44), 10761.

Lee, H.-L.; Dubikovskaya, E. A.; Hwang, H.; Semyonov, A. N.; Wang, H.; Jones, L. R.; Twieg, R. J.; Moerner, W. E.; Wender, P. A. *J. Am. Chem. Soc.* 2008, 130 (29), 9364.

Sandvig, K.; Olsnes, S. *J. Biol. Chem.* 1982, 257(13), 7504.

Rin Jean, S.; Tulumello, D. V.; Wisnovsky, S. P.; Lei, E. K.; Pereira, M. P.; Kelley, S. O. *ACS Chem. Biol.* 2014, 9 (2), 323.

Fonseca, S. B.; Pereira, M. P.; Mourtada, R.; Gronda, M.; Horton, K. L.; Hurren, R.; Minden, M. D.; Schimmer, A. D.; Kelley, S. O. *Chem. Biol.* 2011, 18 (4), 445.

Dubikovskaya, E. A.; Thorne, S. H.; Pillow, T. H.; Contag, C. H.; Wender, P. A. *Proc. Natl. Acad. Sci.* 2008, 105 (34), 12128.

Wender, P. A.; Galliher, W. C.; Bhat, N. M.; Pillow, T. H.; Bieber, M. M.; Teng, N. N. H. *Gynecol. Oncol.* 2012, 126 (1), 118.

Saito, G.; Swanson, J. A.; Lee, K.-D. *Adv. Drug Deliv. Rev.* 2003, 55 (2), 199.

Wang, Y. C.; Juric, D.; Francisco, B.; Yu, R. X.; Duran, G. E.; Chen, G. K.; Chen, X.; Sikic, B. I. Genes. *Chromosomes Cancer* 2006, 45 (4), 365.

General Methods. Unless otherwise noted, all air- and moisture-sensitive reactions were carried out in glassware that was flame-dried or oven-dried (>130° C.) cooled under nitrogen ($N_2$). Reaction vessels were sealed with rubber septa or Teflon-coated caps and maintained in an inert environment under a positive pressure of anhydrous $N_2$. Stirring was accomplished via magnetic, Teflon®-coated stir bars that were oven-dried and cooled under a nitrogen atmosphere. Solid reagents were measured on a Sartorious CP124S Balance. Air- and moisture-sensitive liquids were transferred via syringe or cannula under an atmosphere of $N_2$. Room temperature indicates an external temperature of 20-25° C. The term in vacuo refers to the use of a rotary evaporator with an attached vacuum membrane pump. Residual solvents were removed using vacuum held at <1.0 Torr.

Materials. Reagents were purchased from Sigma-Aldrich and used as received unless otherwise indicated. 1-(3,5-Bis-trifluoromethyl-phenyl)-3-cyclohexyl-thiourea, guanidinium-functionalized oligocarbonate (9), mercaptobutyric acid, Pyr-SS butyric acid (13), and PTX-C2' Pyr-SS butyric acid conjugate (15) were all prepared according to literature procedures. Unless otherwise noted, all commercial solvents and reagents were used without further purification. Tetrahydrofuran (THF) was distilled from sodium benzophenone ketyl. Dichloromethane ($CH_2Cl_2$) was passed through an alumina drying column (Solv-tek Inc.) using nitrogen pressure. $CH_2Cl_2$ for glove box oligomerizations was stirred over $CaH_2$ overnight, degassed by three freeze-pump-thaw cycles, and vacuum transferred into a flame-dried Schlenk flask. Petroleum ether, pentane, hexane, ethyl acetate (EtOAc), and methanol (MeOH) were obtained from Fisher Scientific. Deuterated solvents were purchased from Cambridge Isotope Laboratories. Paclitaxel was obtained from Hauser Inc. lot number 1001-186 (>99% purity). Octaarginine (Arg8) was obtained from UCB Bioproducts (Batch 3AB3).

Chromatographic Methods. Analytical TLC was performed using 0.25 mm glass-backed silica gel $60F_{254}$-coated plates from EMD Chemicals Inc. and monitored at 254 nm. Plates were visualized by treatment with solutions of p-anisaldehyde or potassium permanganate and gentle heating. Preparative column flash chromatography was performed by running solvent under a pressure of air through silica gel (230-400 mesh, 60 Å), purchased from EMD Chemical Inc. Gel permeation chromatography (GPC) was performed in THF at a flow rate of 1.0 mL/min on a Waters chromatograph equipped with four 5 μm Waters columns (300 mm×7.7 mm) connected in series. A Viscotek S3580 refractive index detector and VE3210 UV/vis detector (310 nm). The system was calibrated using monodisperse polystyrene standards (Polymer Laboratories).

Physical and Spectroscopic Measurements. Nuclear magnetic resonance spectra were taken on a Varian Inova 500 $^1H$ at 500 MHz, $^{13}C$ at 125 MHz) or Varian Mercury 400 ($^1H$ at 400 MHz, $^{13}C$ at 100 MHz, $^{31}P$ at 162 MHz) magnetic resonance spectrometer. Data for $^1H$ NMR spectra are reported as follows: chemical shift, multiplicity (bs=broad singlet, s=singlet, d=doublet, dd=doublet of doublet, t=triplet, q=quartet, m=multiplet), coupling constant (Hz), and integration. Chemical shifts are reported in ppm (δ=units), $^1H$ NMR referenced to residual solvent peak ($CDCl_3$=7.26 ppm or $CD_3OD$=3.31 ppm). $^{13}C$ chemical shifts are reported relative to the solvent ($CDCl_3$=77.1 ppm). $^{31}P$ chemical shifts are reported relative to an external standard ($H_3PO_4$=0 ppm). Infrared spectra were measured on a Perkin-Elmer 1600 Series Fourier transform spectrometer (FTIR), and are reported in wavenumbers ($cm^{-1}$). High-resolution mass spectra (HRMS) were obtained from the Vincent Coates Foundation mass spectrometry laboratory at Stanford University. Matrix-assisted laser desorption/ionization (MALDI) was performed on a Voyager-DE RP MALDI-TOF spectrometer equipped with Delayed Extraction (DE) technology. Samples were ionized in a 2,5-dihydroxybenzoic acid (DHB) matrix. Flow cytometry analysis was performed on a BD Aria LSR-II BD LSRII FACS Analyzer using a 450 nm Violet laser (LSRII.UV, obtained using funds from NIH Shared Instrumentation Grant S10RR027431-01, Stanford University Shared FACS Facility). Confocal Microscopy was conducted on a Leica SP5 CLSM (NCRR Grant S10RR02557401) equipped with a HCX APO L20× water immersion lens. Excitation was achieved through a 488 nm Argon laser tuned to 488 nm (for fluorescein), a HeNe laser tuned to 594 nm (for MitoTracker) and a 594 nm Spectra Physics 15W MaiTai DeepSee 2-photon pulsed laser tuned to 740 nm (For Hoechst 33342).

Cell Culture. Human cervical cancer-derived HeLa cells were obtained as a gift from Prof. Chaitan Khosla. Multidrug-resistant OVCA-429T cells were prepared through selective exposure to paclitaxel over multiple generations, as previously reported. HeLa cells, human ovarian cancer cells (OVCA-429) and murine breast cancer cells (4T1) were cultured in Dulbecco's Modified Eagle Medium (DMEM) containing 10% fetal bovine serum (FBS), 1% Penicillin/Streptomycin (PS) and 1% L-Gluamine. Cells were grown on a 25 $cm^2$ tissue culture flask at 37° C. under an atmosphere containing 5% $CO_2$. Cells were passaged at approximately 80% confluence. Non-adherent Jurkat cells were grown in RPMI media containing 10% fetal bovine serum (FBS) and 1% Penicillin/Streptomycin (PS) in a 25 $cm^2$ tissue culture flask at 37° C. under an atmosphere containing 5% $CO_2$.

Uptake and Toxicity Protocols:

Standard Uptake Procedure. For standard uptake experiments, HeLa cells were plated at 40,000 cells/well in 24-well plates and incubated at 37° C. for 12-24 hours to adhere. Cells were washed with serum-free DMEM prior to treatment. Compounds were diluted from 1 mM stock solutions in PBS to 10 μM treatment concentrations in serum-free DMEM. 400 μL of treatment solution was added to 24-well plate, with each compound being tested in triplicate. Cells were incubated with compound at 37° C. for 10 minutes, before removing media and washing with PBS. 0.4 mL of Trypsin EDTA was added, and cells were incubated for 10 minutes. Trypsin was quenched with 0.6 mL of serum-containing DMEM, and each well was transferred to a 15 mL conical tube and centrifuged at 1200 rpm for 5 minutes. After removal of the supernatant, cells were resuspended in 125 μL of PBS and transferred to FACS tubes and read on a flow cytometry analyzer. Results were analyzed by FlowJo software. Data presented is the mean fluorescence from 10,000 cells analyzed.

Dose Dependent Uptake. Standard uptake procedure was followed, except cells were treated with concentrations of compound from 5 μM to 25 μM. All other conditions remained the same.

Mechanism of Uptake. Standard uptake procedure was followed with the following changes for each mechanistic condition:

High Potassium PBS. Prior to treatment treatment, cells were washed 2× for 5 minutes each with High $K^+$ PBS (136.9 mmol KCl, 1.5 mmol $KH_2PO_4$, and 8.3 mmol $K_2HPO_4$*7 $H_2O$ in 1L DI H2O and titrated to pH=7.2). Compound treatment solutions were also made up in High $K^+$ PBS, and were washed with that buffer before addition of Trypsin EDTA.

PBS with Sodium Azide. Before treatment, cells were washed 2× for 5 minutes each with PBS containing 0.5% (w/v) sodium azide. Compound treatment solutions were also made up in $NaN_3$ PBS, and were washed with that buffer before addition of Trypsin EDTA.

PBS at 4° C. Prior to treatment, cells were washed 2× for 5 minutes each with PBS that had been cooled at 4° C. Compound treatment solutions were pre-cooled at 4° C., and cells were refrigerated at 4° C. for the duration of the 10 minute treatment time. Following treatment, cells were washed with PBS at 4° C. 2× before addition of Trypsin EDTA.

Uptake of Maleimide Conjugates. HeLa cells were plated at 40,000 cells/well in 24-well plates and incubated at 37° C. for 12-24 hours to adhere. Before treatment, a 1:1 molar ratio of thiol-initiated HexPhos oligomer (7) and FL-maleimide (10, Molecular Probes) was incubated for 2 hours in PBS (pH 7.4) at a final concentration of 4 mM. Control conjugate was made my mixing 2-mercaptoethanol with FL-maleimide (10) under the same conditions. Immediately prior to treatment, cells were washed with serum-free DMEM. Conjugates were diluted from 4 mM stock solutions in PBS to 10 µM treatment concentrations in serum-free DMEM. 400 µL of treatment solution was added to 24-well plate, with each conjugate being tested in triplicate. Cells were incubated with compound at 37° C. for 10 minutes, before removing media and washing with PBS. 0.4 mL of Trypsin EDTA was added, and cells were incubated for 10 minutes. Trypsin was quenched with 0.6 mL of serum-containing DMEM, and each well was transferred to a 15 mL conical tube and centrifuged at 1200 rpm for 5 minutes. After removal of the supernatant, cells were resuspended in 125 µL of PBS and transferred to FACS tubes and read on a flow cytometry analyzer for the presence of fluorescein. Results were analyzed by FlowJo software. Data presented is the mean fluorescence from 10,000 cells analyzed.

Confocal Microscopy. HeLa cells were plated in glass-bottom petri dishes (FluoroDish, WPI) at approximately 25% confluence, and incubated at 37° C. for 12 hours to adhere. Cells were washed with serum-free DMEM, and treated with 10 µM FITC-HexPhos conjugate (prepared previously) in serum-free DMEM or 10 minutes at 37° C. One plate of cells was treated 16 hours prior to imaging, and a second immediately before. Following treatment, washed cells 2× with serum-free DMEM that did not contain phenol red indicator. Immediately prior to imaging, cells were incubated with counterstain solution containing 50 nM MitoTracker (from a 1 mM stock in DMSO) and 4 µg/mL Hoescht 33342 (from a 1 mg/mL stock in DMSO) for 20 minutes. Washed cells 2× with serum-free DMEM without phenol red for imaging. Images were taken on a Leica SP5 laser scanning confocal microscope with 2-photon excitation set at 710 nM for Hoescht, and 488 nm and 594 lasers enabled for FITC and MitoTracker respectively. Images were processed using ImageJ (version 1.49) and Pearson's Correlation Coefficient (PCC) calculated using JACoP plugin. Results are the average of 3 experiments containing at least 10 cells each. Control represents the PCC calculated for an image that has been rotated 90°.

MTT Toxicity Assays. The cytotoxicity of HexPhos oligomers, PTX alone, and PTX-HexPhos conjugate (16) were assessed by a standard MTT percent viability assay. Adherent cells (HeLa for oligomers alone, OVCA-429 or OVCA-429T for PTX and PTX-HexPhos conjugate) were plated at 5,000 cells/well in 96 well plates and allowed to incubate at 37° C. for 12-24 hours to adhere. Cells were washed with serum-free DMEM prior to treatment. In a second 96-well plate, compounds were serially diluted over a range of 200 µM to 400 nM, with two-fold dilutions between each well. For PTX conditions, a range of 20 µM to 40 nM was used. Each compound was tested in triplicate. Column 1 had no cells, and column 12 was only treated with serum-free DMEM. Second plate was transferred to the plate containing cells, and incubated at 37° C. for 10 minutes, followed washing and replacement with 150 µL fresh serum-containing DMEM. Cells were incubated for an additional 72 hours at 37° C., after which time cellular viability was assayed by adding µ10 L of 3-(4,5-dimethylthiazol-2-yl)-2,5-diphenyltetrazolium bromide (MTT) solution (15 mg in 3 mL DMEM). Incubated for 2 hours at 37° C. Added 100 µL of solubilizing solution (10% Triton X-100, 90% 0.1 N HCl in isopropanol) to each well and pipetted up and down to solubilize. Incubate for 45 min. Read absorbance on a plate reader at 570 and 690 nm. Subtracted absorbance at 570 from absorbance at 690 and normalized to wells with no cells as a minimum, and untreated cells as a maximum to calculate % viability.

Synthetic Procedures and Characterization Data

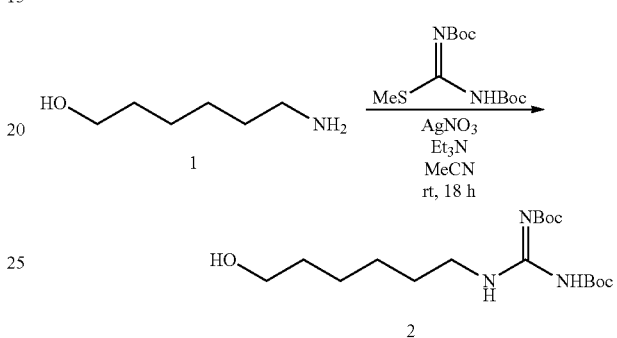

Bis-boc 6-guanidino-1-hexanol (2)

To a solution of 1,3-bis-(tert-butoxycarbonyl)-2-methyl-2-thiopseudourea (4.46 g, 15.4 mmol, 1.2 equiv.) in MeCN (182 mL, 0.07 M) was added 6-aminohexanol (1.50 g, 12.8 mmol, 1 equiv.), and triethylamine (2.7 mL, 19.2 mmol, 1.5 equiv.). In a separate vial, AgNO$_3$ (3.53 g, 2.72 mmol, 1.25 equiv.) was dissolved in 10 mL MeCN. This was added dropwise over the course of 5 minutes. Following addition, the flask was covered in foil and left under N$_2$ overnight. After 18 hours, reaction was diluted with 50 mL EtOAc and filtered over Celite®. The filtrate was concentrated in vacuo, redissolved in EtOAc and was washed with 50 mL each DI H$_2$O (2×), and brine. The organic layer was dried over MgSO$_4$, concentrated, and the resulting oil purified by flash chromatography (50% EtOAC in hexanes) to afford a white solid (4.012 g) in 87% yield.

$^1$H-NMR (400 MHz; CDCl$_3$): δ 8.26-8.23 (m, 1H), 3.53 (d, J=13.1 Hz, 2H), 3.32 (q, J=6.2 Hz, 2H), 2.46-2.34 (m, 1H), 1.49 (m, J=13.9, 7.0 Hz, 4H), 1.38-1.37 (m, 18H), 1.31 (t, J=10.4 Hz, 4H).

$^{13}$-C NMR (101 MHz; CDCl3): δ 163.6, 156.2, 153.4, 83.2, 79.5, 62.6, 41.0, 32.6, 29.1, 28.4, 28.2, 26.8, 25.5

IR (neat) 3332, 3139, 2978, 2933, 1721, 1716, 1633, 1415, 1367, 1334, 1252, 1228, 1156, 1054, 1027 cm$^{-1}$ HRMS: [M]+N$^+$ calculated 382.2318; found, 382.2310.

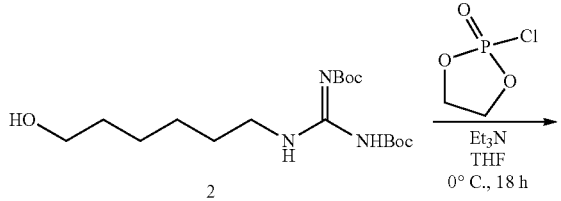

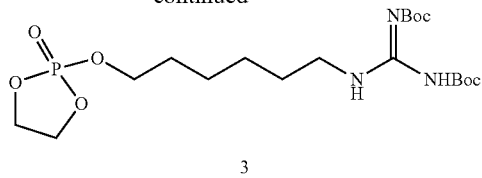

2-(6-bis-boc guanidino hexyloxy)-1,3,2-dioxaphospholane-2-oxide (3)

2-chloro-1,3,2-dioxaphospholane-2-oxide (797 mg, 5.59 mmol, 1.25 eq.) was weighed out into a schlenk flask under an inert $N_2$ atmosphere(glove box). This was placed on ice under nitrogen, and THF (75 mL) was added. In a separate vial, guan hexanol (7.16 g, 20.0 mmol, 1 eq.) was dissolved in THF (10 mL) and triethylamine (2.8 mL, 20 mmol, 1 eq) was added. Vial contents were added via syringe to schlenk flask dropwise over the course of 10 minutes and allowed to react for 20 hours. Following reaction, product was filtered over a pad of Celite®. Crude product was dissolved in a small amount (5 mL) THF and triturated with 20 mL dry pentane. Product oiled out in a −55° C. freezer overnight. Removed pentane layer and dried under vacuum for 10 hours to afford pure product as a slightly-yellow oil (79% yield).

$^1$H-NMR (400 MHz, CDCl$_3$): δ 11.43 (s, 1H), 8.23 (s, J=4.4 Hz, 1H), 4.39-4.28 (m, 4H), 4.08-4.03 (m, 2H), 3.33 (q, J=6.3 Hz, 2H), 1.63 (quintet, J=6.9 Hz, 2H), 1.50 (q, J=7.0 Hz, 2H), 1.42 (s, 18H), 1.33 (t, J=3.3 Hz, 4H).
$^{13}$C-NMR (101 MHz, CDCl$_3$): δ 163.75, 156.27, 153.44, 83.23, 79.36, 69.11, 69.05, 66.19, 66.16, 40.88, 30.34, 30.28, 29.00, 28.45, 28.22, 28.14, 26.50, 25.22.
$^{31}$P-NMR (162 MHz, CDCl$_3$): δ 18.64.
IR (neat) 3326, 2977, 2930, 1720, 1638, 1414, 1367, 1331, 1281, 1251, 1227, 1156, 1134, 1029 cm$^{-1}$
HRMS: [M+H]$^+$ calculated 466.2318; found, 466.2310.

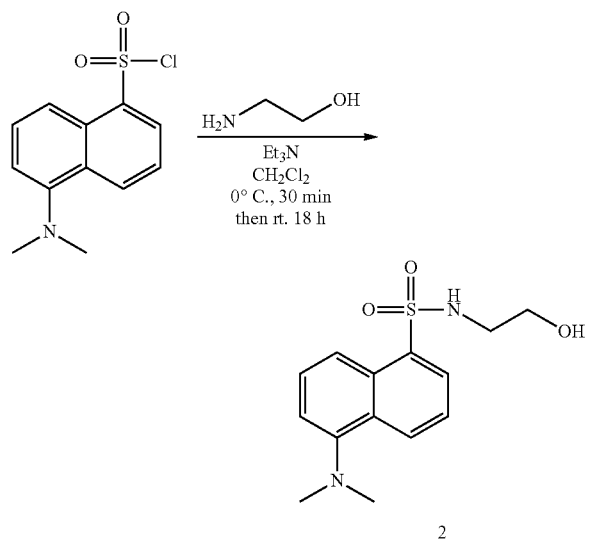

5-(dimethylamino)-N-(2-hydroxyethyl)naphthalene-1-sulfonamide (Dansyl) initiator (4)

Dansyl chloride (962 mg, 3.57 mmol, 1 eq) dissolved in CH$_2$Cl$_2$ (26 mL, 0.15M) in a dry round-bottom flask purged with nitrogen and placed on ice. Ethanolamine (240 mg, 3.92 mmol, 1.1 eq) and triethylamine (0.6 mL, 4.28 mmol, 1.2 eq) were dissolved a small amount of CH$_2$Cl$_2$ in a separate vial. This was added dropwise to the solution of dansyl chloride over the course of 10 minutes. The reaction was left at 0° C. for 30 minutes and then warmed to room termpearture for 8 hours. Following reaction, washed crude mixture with H2O, brine, dried over MgSO$_4$ and concentrated. Purified by flash chromatography (5-10% MeOH in CH$_2$Cl$_2$) to give dansyl initiator (7) as a yellow-green solid in 68% yield.

$^1$H NMR (400 MHz, Chloroform-d) δ 8.53 (dt, J=8.6, 1.1 Hz, 1H), 8.30 (dt, J=8.7, 0.9 Hz, 1H), 8.22 (dd, J=7.3, 1.3 Hz, 1H), 7.51 (ddd, J=9.7, 8.6, 7.4 Hz, 2H), 7.15 (dd, J=7.6, 0.9 Hz, 1H), 5.81 (t, J=6.1 Hz, 1H), 3.60 (t, J=5.0 Hz, 2H), 3.02 (td, J=5.9, 4.8 Hz, 2H), 2.87 (s, 6H).
$^{13}$C NMR (101 MHz, Chloroform-d) δ 152.11, 134.65, 130.77, 130.07, 129.78, 129.77, 128.77, 123.44, 118.98, 115.54, 61.56, 45.66, 45.55.
IR (neat) 3496, 3294, 2943, 2788, 1611, 1587, 1454, 1353, 1231, 1143, 1093, 1060, 940 cm$^{-1}$

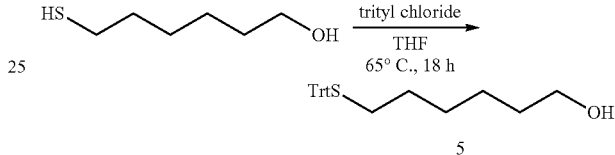

6-(tritylthio)hexan-1-ol (6)

Trityl chloride (4.56 g, 16.4 mmol, 1.1 eq) was dissolved in anhydrous THF (15 mL, 1 M) in a round bottom flask. 6-mercapto-1-hexanol (2 g, 15 mmol, 1 eq) was added and the flask was placed on an oil bath at 65° C. for 18 hours. Following reaction, volitiles were removed under reduced pressure and reaction was purified by column chromatography (30% EtOAc in Hexanes) to afford trityl-mercaptohexanol (##) as a white solid in >98% yield.

$^1$H NMR (500 MHz, Chloroform-d) δ 7.49-7.39 (m, 6H), 7.29 (t, J=7.7 Hz, 6H), 7.25-7.18 (m, 3H), 3.58 (t, J=6.6 Hz, 2H), 2.16 (t, J=7.3 Hz, 2H), 1.54 (s, 1H), 1.53-1.45 (m, 2H), 1.45-1.38 (m, 2H), 1.34-1.18 (m, 4H).
$^{13}$C NMR (126 MHz, Chloroform-d) δ 145.29, 129.94, 129.86, 128.10, 126.80, 66.66, 63.11, 32.76, 32.17, 29.01, 28.81, 25.57.
IR (neat) 3350, 3055, 2929, 2855, 1594, 1488, 1443, 1183, 1080, 1053, 1033 cm$^{-1}$

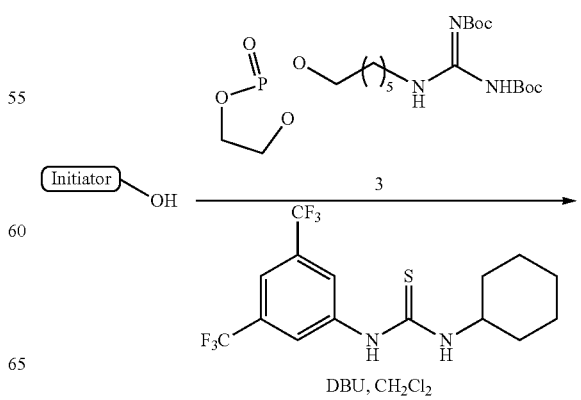

-continued

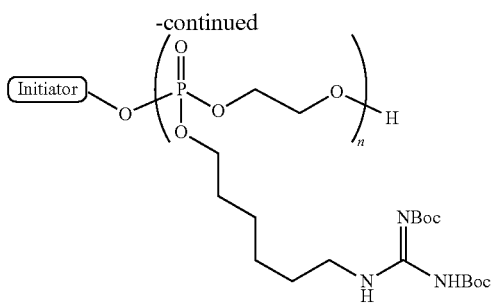

HexPhos oligomerization reactions (general procedure). In a glove box under $N_2$ atmosphere (<10 ppm $O_2$), initiator (6 or 7, 1 equiv) was weighed out, along with thiourea catalyst (5 mol % relative to monomer) into a pre-aliquotted vial containing HexPhos monomer (n equivalents relative to initiator) and a stir bar. Dichloromethane was added to a final monomer concentration of 1M. Oligomerization was initiated by addition of DBU (5 mol % relative to monomer) neat. Reaction was stirred at room temperature for 2 hours to allow for complete conversion. Following reaction, catalysts were quenched by addition of approximately 10 mg of benzoic acid as a solid. Vial was removed from the glove box, and crude oligomer was purified by dialysis (regenerated cellulose, 1000 Da MWCO, SpectraPor) against 1 L of methanol for approximately 18 hours, changing the methanol after 8 hours. Solvent was evaporated to afford oligomers as green waxy solids. Degree of polymerization (DP) was determined by $^1$H NMR endgroup analysis, and molecular weights and dispersity ($M_w/M_n$) confirmed by gel permeation chromatography (GPC).

Protected Dansyl-HexPhos8 (6a)

$^1$H NMR (400 MHz, $CDCl_3$) δ 8.47 (d, 1H), 8.27 (m, 8H), 8.16 (d, 1H), 7.50 (m, 2H), 7.13 (d, 1H), 4.22-4.03 (m, 48H), 3.76 (bs, 16H) 3.36 (bs, 2H), 2.84 (s, 6H), 1.66 (bs, 17H), 1.54 (bs, 17H), 1.45 (bs, 121H), 1.34 (bs, 30H).
$^{31}$P NMR (162 MHz, $CDCl_3$) δ −0.20.

Protected Dansyl-HexPhos10 (6b)

$^1$H NMR (400 MHz, $CDCl_3$) δ 8.46 (d, 1H), 8.26 (bs, 10H), 8.16 (d, 1H), 7.47 (m, 2H), 7.14 (d, 1H), 4.21-4.02 (m, 62H), 3.73 (bs, 3H), 3.35 (bs, 20H), 3.13 (bs, 2H), 2.83 (s, 6H), 1.65 (bs, 22H), 1.53 (bs, 23H), 1.44 (bs, 156H), 1.33 (40H).
$^{31}$P NMR (162 MHz, $CDCl_3$) δ −0.16.

Protected Dansyl-HexPhos12 (6c)

$^1$H NMR (400 MHz, $CDCl_3$) δ 8.50 (d, 1H), 8.29 (bs, 1H), 8.17 (d, 1H), 7.49 (m, 2H), 7.16 (d, 1H), 4.23-4.05 (m, 65H), 3.77 (bs, 3H), 3.37 (bs, 21H), 3.15 (bs, 2H), 2.85 (s, 6H), 1.67 (bs, 24H), 1.55 (bs, 22H), 1.47 (bs, 167H), 1.36 (bs, 43H).
$^{31}$P NMR (162 MHz, $CDCl_3$) δ −0.14.

Protected Dansyl-HexPhos16 (6d)

$^1$H NMR (400 MHz, $CDCl_3$) δ 8.46 (d, 1H), 8.26 (bs, 17H), 8.15 (d, 1H), 7.47 (m, 2H), 7.12 (d, 1H), 4.20-4.02 (bs, 114H), 3.73 (bs, 3H), 3.35 (bs, 36H), 3.12 (bs, 2H), 2.81 (s, 6H), 1.64 (bs, 42H), 1.43 (bs, 240H), 1.33 (bs, 76H).
$^{31}$P NMR (162 MHz, $CDCl_3$) δ −0.15.

Protected Dansyl-HexPhos25 (6e)

$^1$H NMR (400 MHz, $CDCl_3$) δ 8.49 (d, 1H), 8.27 (bs, 24H), 8.16 (d, 1H), 7.51 (m, 2H), 7.13 (d, 1H), 4.22-4.03 (bs, 160H), 3.75 (bs, 5H), 3.36 (bs, 53H), 3.14 (bs, 2H), 2.84 (s, 6H), 1.66 (bs, 61H), 1.54 (bs, 58H), 1.45 (bs, 428H), 1.35 bs, 110H).
$^{31}$P NMR (162 MHz, $CDCl_3$) δ −0.11.

Protected TrtS-HexPhos8 (7)

$^1$H NMR (400 MHz, $CDCl_3$) δ 8.27 (bs, 8H), 7.26 (m, 17H), 4.21-4.03 (m, 53H), 3.76 (bs, 3H), 3.37 (m, 17H), 2.10 (t, 2H), 1.66 (bs, 20H), 1.54 (bs, 20H), 1.46 (s, 140H), 1.35 (bs, 37H).
$^{31}$P NMR (162 MHz, $CDCl_3$) δ −0.11.

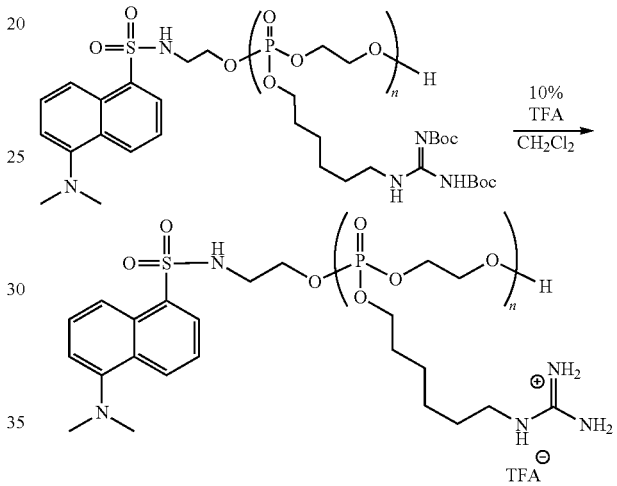

HexPhos Deprotection Reaction for Dansyl-Initiated Oligomers

Oligomers (approximately 200 mg, 0.1 mmol) were dissolved in 4.5 mL dichloromethane in a glass vial with a stir bar. Trifluoroacetic acid (0.5 mL) was added via syringe, and the vial was sealed under nitrogen. Deprotection reaction was stirred at room temperature for 12 hours, after which time volatiles were was evaporated to afford deprotected oligomers in >99% yield as thick oils.

Deprotected Dansyl-HexPhos8 (6a)

$^1$H NMR (400 MHz, $CD_3OD$) δ 8.66 (bs, 1H), 8.56 (bs, 1H), 8.31 (bs, 1H), 7.76 (m, 3H), 4.30-4.13 (m, 50H), 3.72 (m, 5H), 3.17 (bs, 17H), 1.73 (bs, 17H), 1.59 (bs, 16H), 1.43 (bs, 32H).
$^{31}$P NMR (162 MHz, $CD_3OD$) δ −0.66.

Deprotected Dansyl-HexPhos10 (6b)

$^1$H NMR (400 MHz, $CD_3OD$) δ 8.59 (m, 2H), 8.29 (m, 1H), 7.74 (m, 3H), 4.30-4.13 (m, 62H), 3.74 (bs, 6H), 3.30, 3.17 (bs, 35H), 1.86 (bs, 2 h,), 1.74 (bs, 22H), 1.59 (bs, 20H), 1.43 (bs, 42H).
$^{31}$P NMR (162 MHz, $CD_3OD$) δ −0.65.

Deprotected Dansyl-HexPhos12 (6c)

$^1$H NMR (400 MHz, CD$_3$OD) δ 8.56 (d, 2H), 8.50 (m, 1H), 8.25 (d, 1H), 7.69 (t, 2H), 7.55 (m, 1H), 4.30-4.13 (m, 65H), 3.72 (m, 6H), 3.17 (m, 21H), 3.07 (s, 6H), 1.87 (m, 4H), 1.72 (bs, 23H), 1.60 (bs, 22H), 1.43 (bs, 45H).
$^{31}$P NMR (162 MHz, CD$_3$OD) δ −0.65.

Deprotected Dansyl-HexPhos16 (6d)

$^1$H NMR (400 MHz, CD$_3$OD) δ 8.56 (m, 2H), 8.26 (m, 1H), 7.70 (m, 3H), 4.30-4.13 (m, 68H), 3.74 (m, 4H), 3.17 (m, 27H), 1.87 (m, 1H), 1.74 (bs, 25H), 1.60 (bs, 22H), 1.43 (bs, 46H).
$^{31}$P NMR (162 MHz, CD$_3$OD) δ −0.64.

Deprotected Dansyl-HexPhos25 (6e)

$^1$H NMR (400 MHz, cd$_3$od) δ 8.56 (d, 1H), 8.44 (d, 1H), 8.24 (d, 1H), 7.65 (t, 2H), 7.43 (m, 1H), 4.30-4.13 (m, 169H), 3.75 (bs, 7H), 3.18 (m, 52H), 2.98 (s, 6H), 1.74 (bs, 60H), 1.60 (bs, 56H), 1.43 (bs, 119H).
$^{31}$P NMR (162 MHz, CD$_3$OD) δ −0.65.

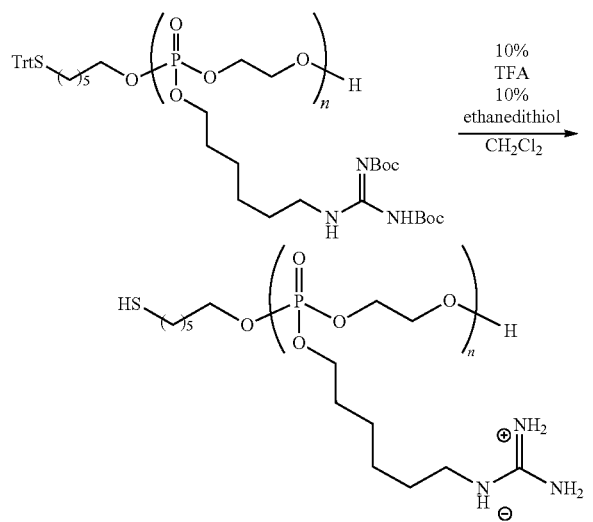

HexPhos Deprotection for Trityl-Thiol-Initiated Oliqomers

Trityl-thiol initiated oligomers (approximately 200 mg, 0.1 mmol) were dissolved in 4.5 mL dichloromethane in a glass vial with a stir bar. Ethanedithiol (0.5 mL, 10% v/v) was added as a cation scavenger. Trifluoroacetic acid (0.5 mL) was added via syringe, and the vial was sealed under nitrogen. Deprotection reaction was stirred at room temperature for 12 hours, after which time volatiles were evaporated. Crude oligomers were dissolved in a small amount of methanol and precipitated 3× from cold diethyl ether (20 mL each time) and collected by centrifugation to afford deprotected oligomers in >99% yield as thick oils.

Deprotected TrtS-HexPhos8 (7)

$^1$H NMR (400 MHz, CD$_3$OD) δ 4.31 (bs, 35H), 4.14 (m, 24H), 3.75 (bs, 3H), 3.18 (m, 17H), 2.55 (m, 2H), 1.75 (bs, 23H), 1.61 (bs, 22H), 1.44 (bs, 45H).
$^{31}$P NMR (162 MHz, CD$_3$OD) δ −0.63.

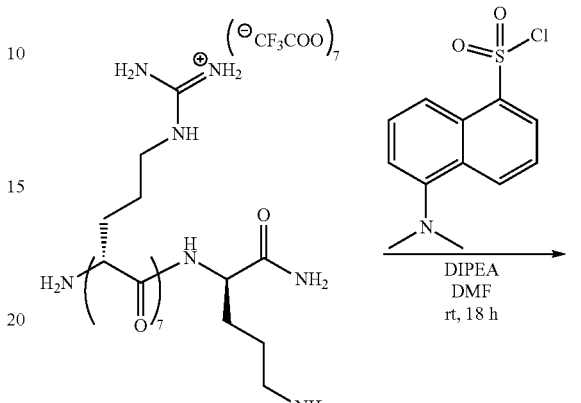

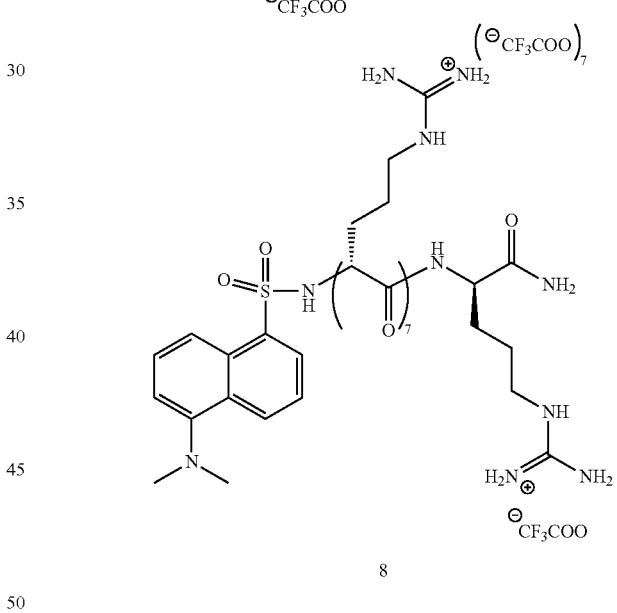

Octaarginine (39.7 mg, 0.02 mmol, 1 eq) was weighed out into a 2-dram vial and dissolved in a small amount of DMF (200 uL). Dansyl chloride (7.69 mg, 0.028 mmol, 1.5 eq) was dissolved in DMF (400 uL) and added to octaarginine in a single portion. DIPEA (33 uL, 0.19 mmol, 10 eq) was added and the reaction was covered in foil and allowed to stir overnight. Following reaction, blew off DMF under a stream of N$_2$ and purified by reverse-phase HPLC (5-70% CH$_3$CN w/0.1% TFA in 30 minutes). Lyophilized product-containing fractions to afford Dansyl-Arg$_8$ as a white fluffy solid.
$^1$H-NMR (400 MHz, D$_2$O): δ 8.60 (d, J=8.8 Hz, 1H), 8.30 (d, J=8.8 Hz, 3H), 8.23 (d, J=7.4 Hz, 1H), 7.89 (d, J=7.9 Hz, 1H), 7.73 (q, J=8.6 Hz, 2H), 4.13-4.03 (m, 7H), 3.43-3.40 (m, 1H), 3.28 (s, 6H), 3.02-2.97 (m, 14H), 2.60-2.55 (m, 1H), 2.45-2.41 (m, 1H), 1.68-1.31 (m, 31H), 0.99 (s, 1H), 0.75 (s, 1H).

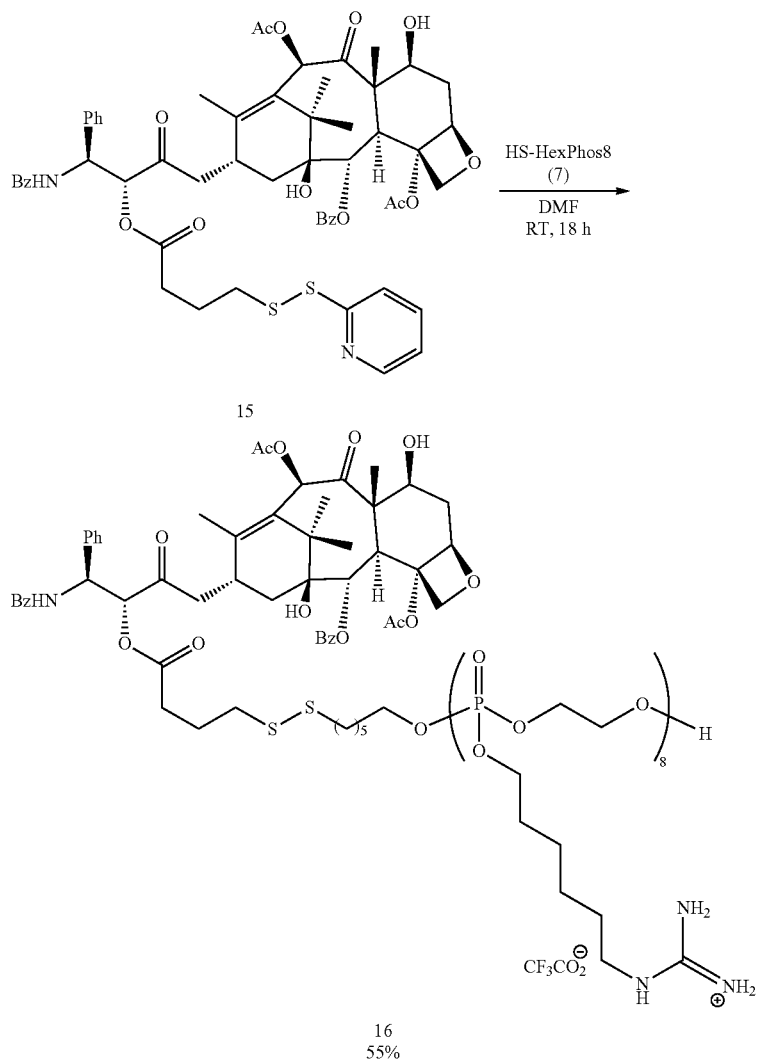

Paclitaxel-HexPhos Coniuqate (16)

In a dry vial with a stir bar was added HS-HexPhos8 oligomer (7, 19.4 mg, 0.0061 mg, 1 equiv) dissolved in a small amount of DMF (0.15 mL). Taxol C2'-SSPyr³ (6.52 mg, 0.0061 mg, 1 equiv) dissolved in DMF (0.15 mL) was added for a final concentration of 0.02 M. Vial was sealed under nitrogen, and allowed to react for 18 hours. Following reaction, added 1.5 mL methanol and purified by semi-prep RP-HPLC (10-90% CH$_3$CN in H$_2$O w/0.1% TFA). Fractions containing conjugate were pooled and lyophilized to afford product as a thick sticky oil (55%). Incorporation of PTX was calculated by relative endgroup integrations by $^1$H NMR.

$^1$H NMR (400 MHz, CD$_3$OD) δ 8.11 (d, J=7.7 Hz, 2H), 7.83 (d, J=7.8 Hz, 2H), 7.77-7.32 (m, 11H), 7.27 (t, J=7.1 Hz, 1H), 6.45 (s, 1H), 6.04 (d, J=9.2 Hz, 1H), 5.79 (s, 1H), 5.62 (d, J=7.1 Hz, 1H), 5.46 (d, J=6.9 Hz, 1H), 5.00 (d, J=9.7 Hz, 1H), 4.30 (m, J=4.4 Hz, 49H), 4.13 (m, J=6.8, 6.2 Hz, 36H), 3.82 (d, J=11.7 Hz, 2H), 3.75 (d, J=5.1 Hz, 4H), 3.18 (m, J=7.2 Hz, 28H), 2.68 (m, J=14.1, 7.1 Hz, 4H), 2.59-2.48 (m, 2H), 2.38 (s, 3H), 2.17 (s, 3H), 2.03 (t, J=7.1 Hz, 1H), 1.93 (d, J=2.6 Hz, 3H), 1.86-1.52 (m, 74H), 1.44 (s, 82H), 1.14 (s, 3H), 1.12 (s, 3H).
$^{31}$P NMR (162 MHz, CD$_3$OD) δ −0.34, −0.63

Dove, A. P.; Pratt, R. C.; Lohmeijer, B. G. G.; Waymouth, R. M.; Hedrick, J. L. Thiourea-Based Bifunctional Organocatalysis: Supramolecular Recognition for Living Polymerization. J. Am. Chem. Soc. 2005, 127 (40), 13798-13799.

Cooley, C. B.; Trantow, B. M.; Nederberg, F.; Kiesewetter, M. K.; Hedrick, J. L.; Waymouth, R. M.; Wender, P. A. Oligocarbonate Molecular Transporters: Oligomerization-Based Syntheses and Cell-Penetrating Studies. J. Am. Chem. Soc. 2009, 131 (45), 16401-16403.

Dubikovskaya, E. A.; Thorne, S. H.; Pillow, T. H.; Contag, C. H.; Wender, P. A. Overcoming Multidrug Resistance of Small-Molecule Therapeutics through Conjugation with Releasable Octaarginine Transporters. Proc. Natl. Acad. Sci. 2008, 105 (34), 12128-12133.

Wang, Y. C.; Juric, D.; Francisco, B.; Yu, R. X.; Duran, G. E.; Chen, G. K.; Chen, X.; Sikic, B. I. Regional Activation of Chromosomal Arm 7q with and without Gene Amplification in Taxane-Selected Human Ovarian Cancer Cell Lines. Genes. Chromosomes Cancer 2006, 45 (4), 365-374.

Bolte, S.; Cordelières, F. P. A Guided Tour into Subcellular Colocalization Analysis in Light Microscopy. J. Microsc. 2006, 224 (3), 213-232.

What is claimed is:

1. A transporter compound of the formula:

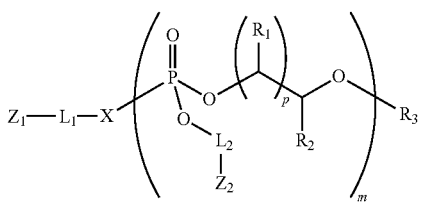

wherein:
$Z_1$ is a cytotoxic or a cytostatic agent;
$L_1$ is an optional linker;
X is O, S or NH;
$L_2$ is a linker;
$Z_2$ is an guanidine group or a protected guanidine group;
$R_3$ is H, an alkyl, a substituted alkyl, an acyl, a substituted acyl, an aryl, a substituted aryl, a heteroaryl or a substituted heteroaryl;
$R_1$ and $R_2$ are independently H, an alkyl or a substituted alkyl;
each p is independently 1, 2 or 3; and
m is between 2 and 50.

2. A transporter compound of the formula:

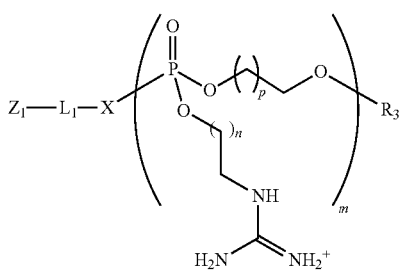

wherein:
$Z_1$ is a cytotoxic or cytostatic agent;
$L_1$ is an optional linker;
X is O, S or NH;
$R_3$ is H, an alkyl, a substituted alkyl, an acyl, a substituted acyl, an aryl, a substituted aryl, a heteroaryl or a substituted heteroaryl;
p is 1, 2 or 3; and
wherein n is 1 to 25 and m is 5 to 30.

3. The transporter compound of claim 2, wherein:
$R_3$ is H;
X is O;
p is 1; and
n is 4 to 10.

4. The transporter compound of claim 1, wherein $L_1$ is a cleavable linker.

5. A method of delivering a cytotoxic or cytostatic agent to a cancer cell, the method comprising
Contacting the cell with a transporter compound of the formula:

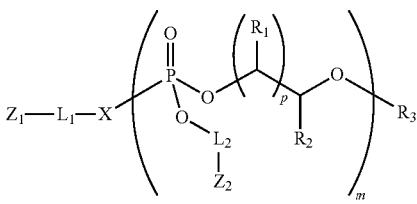

wherein:
$Z_1$ is a cytotoxic or cytostatic agent;
$L_1$ is an optional linker;
X is O, S or NH;
$L_2$ is a linker;
$Z_2$ is guanidine group or a protected guanidine group;
$R_3$ is H, an alkyl, a substituted alkyl, an acyl, a substituted acyl, an aryl, a substituted aryl, a heteroaryl or a substituted heteroaryl;
$R_1$ and $R_2$ are independently H, an alkyl or a substituted alkyl;
p is 1, 2 or 3; and
m is between 2 and 50;
under conditions to deliver the agent to the cell.

6. The method of claim 5, wherein $L_1$ is a cleavable linker and the method further comprises cleaving $L_1$ to release the agent.

7. A pharmaceutical composition comprising the composition of claim 1, and a pharmaceutically acceptable excipient.

8. A method of treating a subject suffering from cancer, the method comprising administering to the subject an effective amount of the composition of claim 7; to treat the subject.

9. The method according to claim 5, wherein the cancer cell is a drug resistant cancer cell.

10. The method according to claim 9, wherein the drug resistant cancer cell is a paclitaxel-resistant cancer cell.

11. The method according to claim 8 wherein the cancer is selected from the group consisting of colon cancer, prostate cancer, breast cancer, melanoma cancer, ductal cancer, endometrial cancer, stomach cancer, cancer of the dysplastic oral mucosa, invasive oral cancer, non-small cell lung carcinoma, transitional and squamous cell urinary carcinoma, neuroblastoma, glioma, childhood acute leukemia, non-Hodgkin's lymphoma, chronic lymphocytic leukemia, malignant cutaneous T-cell, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, myelogenous leukemia, chronic myelogenous leukemia, acute lymphocytic leukemia, Hodgkin's lymphoma, non-Hodgkin's lymphoma, multiple myeloma, ovarian cancer, breast cancer, soft tissue sarcoma and renal cell carcinoma.

12. The method according to claim 8, herein the cancer is breast cancer, ovarian cancer, non-small-cell lung cancer, soft tissue sarcoma and lymphoma.

13. The method according to claim 8, wherein the cancer is a paclitaxel resistant cancer.

14. The method according to claim 13, wherein the cancer is ovarian cancer.

* * * * *